US012642275B2

(12) United States Patent
Louvet-Pommier et al.

(10) Patent No.: US 12,642,275 B2
(45) Date of Patent: Jun. 2, 2026

(54) ANTIMICROBIAL LIQUID COMPOSITION AND USE THEREOF AS A PRESERVATIVE ACTIVATOR IN COSMETIC PRODUCTS

(71) Applicant: ROQUETTE FRERES, Lestrem (FR)

(72) Inventors: Géraldine Louvet-Pommier, Lachelle (FR); Léon Mentink, Lille (FR); Daniel Wils, Morbecque (FR); Nicolas Tesse, Vaucresson (FR)

(73) Assignee: ROQUETTE FRERES, Lestrem (FR)

( * ) Notice: Subject to any disclaimer, the term of this patent is extended or adjusted under 35 U.S.C. 154(b) by 357 days.

(21) Appl. No.: 18/256,365

(22) PCT Filed: Dec. 10, 2021

(86) PCT No.: PCT/EP2021/025490
§ 371 (c)(1),
(2) Date: Jun. 7, 2023

(87) PCT Pub. No.: WO2022/122187
PCT Pub. Date: Jun. 16, 2022

(65) Prior Publication Data
US 2024/0023559 A1 Jan. 25, 2024

(30) Foreign Application Priority Data
Dec. 10, 2020 (FR) .................................... 2013020
Mar. 29, 2021 (FR) .................................... 2103219

(51) Int. Cl.
*A01N 65/44* (2009.01)
*A01N 37/36* (2006.01)
*A01N 43/16* (2006.01)
*A01P 1/00* (2006.01)
*A01P 3/00* (2006.01)
*A61K 8/06* (2006.01)
*A61K 8/34* (2006.01)
*A61K 8/36* (2006.01)
*A61K 8/365* (2006.01)
*A61K 8/368* (2006.01)
*A61K 8/60* (2006.01)
*A61K 8/9794* (2017.01)
*A61Q 5/02* (2006.01)

(52) U.S. Cl.
CPC ............. *A01N 65/44* (2013.01); *A01N 37/36* (2013.01); *A01N 43/16* (2013.01); *A01P 1/00* (2021.08); *A01P 3/00* (2021.08); *A61K 8/062* (2013.01); *A61K 8/34* (2013.01); *A61K 8/36* (2013.01); *A61K 8/365* (2013.01); *A61K 8/368* (2013.01); *A61K 8/602* (2013.01); *A61K 8/9794* (2017.08); *A61Q 5/02* (2013.01); *A61K 2800/524* (2013.01)

(58) Field of Classification Search
CPC ........ A01N 65/44; A01N 31/04; A01N 37/06; A01N 37/10; A01N 37/36; A01N 39/00; A01N 43/16; A01P 1/00; A01P 3/00; A61K 8/062; A61K 8/34; A61K 8/36; A61K 8/365; A61K 8/368; A61K 8/602; A61K 8/9794; A61K 2800/524; A61Q 5/02
See application file for complete search history.

(56) References Cited

U.S. PATENT DOCUMENTS

2015/0118172 A1 4/2015 Rudolph et al.
2015/0265666 A1 9/2015 Modak et al.

FOREIGN PATENT DOCUMENTS

KR 20150097560 A 8/2015

*Primary Examiner* — Quanglong N Truong

(57) ABSTRACT

The present application relates to the use of an antimicrobial composition comprising essentially ingredients of natural origin as a preservative activator in cosmetic products. Due to the selection of the components of this antimicrobial composition, it has very broad compatibility with most formulations of cosmetic products, and may in particular be integrated into these formulations without destabilizing them or having to modify them, while maintaining the transparency of said cosmetic products.

7 Claims, 3 Drawing Sheets

Escherichia coli – ATCC® 8739 / TSB (R1)

■ T0h ▨ T0.5h ▨ T24h ☐ T48h

Candida albicans – ATCC® 10231 / YM (R1)

■ T0h ▨ T0.5h ▨ T24h ☐ T48h

ANTIMICROBIAL LIQUID COMPOSITION AND USE THEREOF AS A PRESERVATIVE ACTIVATOR IN COSMETIC PRODUCTS

TECHNICAL FIELD

The invention relates to the field of the preservation of cosmetic products, and more specifically to the field of preservative activators in cosmetic products.

PRIOR ART

In recent years, the cosmetics industry has been faced with a situation that is increasingly difficult in a field just as essential as the effectiveness of cosmetic products itself, namely, the preservation of cosmetic products, in the microbiological sense of the term. Cosmetic products are aqueous media that are conducive to the development of bacteria, fungi and yeasts. To guarantee consumer safety, molecules or compounds having antibacterial and antifungal activities must be added to cosmetic products. Regulations strictly govern the nature of these molecules or compounds, as well as the doses wherein they can be added to cosmetic products, such as for example in France in the cosmetic Regulation No. 1223/2009 in appendix 5 entitled "List of preservatives allowed in cosmetic products", which includes sixty authorized preservatives.

In fact, the number of authorized preservatives that are actually used by producers of cosmetic products is much smaller, and close to about fifteen preservatives. Preservatives that are universally used can be counted on the fingers of one hand. Producers are limited to these preservatives either because they anticipate regulation changes, or because they need to meeting consumer expectations to have the most clean or natural cosmetic products possible.

In order to satisfy this consumer expectation, the producers of cosmetic products will go even further in trying to reduce the amount of preservatives to its minimum, or even to a value below its known minimum dose, and by associating it with other molecules or compounds called "preservative activators" in order to obtain a preservative effect. These "preservative activator" are not preservatives listed as such, but have activities, in particular antimicrobial activities, which complete or increase the antimicrobial activity of preservatives.

Essential oils are widely known for their antibacterial and antifungal activities. Many patents have attempted to associate them with other ingredients.

The Lonza WO 2014/014416 patent teaches antimicrobial compositions composed of a preservative and a potentiating of said preservative. The preservative may be selected from a multitude of compounds, ranging from cinnamaldehyde to sorbic acid or benzoic acid, to essential oils of wintergreen or citronella. The potentiator may be chosen from erythorbic acid or gluconic acid, or salts thereof. Regarding gluconic acid, its cyclic form, known as gluconolactone, is preferred. Citronella oil is cited in this application, and the antibacterial activity data presented shows that this essential oil does not have sufficient activity to act as a preservative or as a preservative activator. Many additives are mentioned in this application, including solubilizers, without any indication being given as regards their nature or their usefulness for the composition or for the cosmetic formulation.

The CleanWell patent U.S. Pat. No. 6,346,281 proposes combining essential oil of citronella with metal ions, such as copper sulfate, and with a "biosurfactant" and a solvent. The "biosurfactant" may be either "BOD", or Tween-80, which is a polyethoxylated sorbitan. The solvent may be chosen from organic solvents such as ethanol. According to another Cleanwell patent WO 2010/059399, the combination of thyme oil with Cu2+ ions and an alkylpolyglucoside makes it possible to obtain a composition capable of foaming, useful for the treatment and prevention of bacterial infections resistant to antibiotics, in particular methicillin-resistant *Staphylococcus aureus.*

The Reckitt Benckize U.S. Pat. No. 5,403,587 combines essential oil of thyme or citronella with an ethoxylated fatty acid, a "nonoxynol-10" carboxylic acid, or a sodium salt of coconut fatty acid, and with a surfactant and an organic solvent. The surfactant and the organic solvent are essential to provide a composition in liquid form capable of being dispersed or solubilized. The surfactant may be selected from anionic or amphoteric surfactants. These combinations exhibit an anti-bacterial activity on *S. aureus* and on *P. aeruginosa.*

The Procter & Gamble patent WO 2008/126057 discloses antimicrobial compositions for mouth care. They comprise a mixture of essential oils containing acyclic compounds and cyclic compounds. The addition of gluconic acid is recommended for its chelating power of calcium ions located on the walls of the bacteria, which helps to improve the bactericidal power of the composition. As additives, the composition may comprise all surfactants, but anionic surfactants, cationic surfactants, or zwitterionic surfactants are preferred. Nonionic surfactants are also cited, and the nonionic surfactants prepared by condensation of alkylene oxide, that is polyethoxylated nonionic surfactants.

Indusco U.S. Pat. No. 9,687,002 proposes to put essential oil from citronella in a microemulsion in water with added citric acid, lactic acid or acetic acid as a pH buffer. The microemulsion is obtained by means of at least two surfactants having an HLB between 9 and 18, and these surfactants may be nonionic surfactants. The microemulsion makes it possible to obtain a stable composition, that is, remaining macroscopically homogeneous, and transparent.

L'Oreal FR3061010 discloses essential oil nanoemulsions obtained by emulsifying these essential oils in a mixture of water and water-soluble organic solvent by surfactants chosen from anionic, nonionic, amphoteric, zwitterionic or cationic surfactants. These nanoemulsions are prepared for their topical use for the treatment of bacterial or fungal infections. Essential oil of citronella is presented although no antimicrobial activity is attributed to it. Among the nonionic surfactants, alkyl polyglucosides are preferred, and particularly caprylyl/capryl glucoside, such as Oramix™ CG110 from Seppic. In the sole example of this patent, Oramix™ CG110 is formulated with ten essential oils, ethanol and water. The amount of Oramix™ CG110 used y is 0.05% by weight relative to the total weight of the formulation. Generally, L'Oréal FR3061010 recommends using an amount of nonionic surfactant of less than 1% by weight relative to the total weight of the nanoemulsion. It is the combination of a nonionic surfactant and ethanol that makes it possible to obtain a nanoemulsion. This nanoemulsion state has advantages in terms of texture, softness to the touch, and transparency.

According to Nestec WO 2012/072488, located in the field of food, the emulsification of essential oils makes it possible to increase their effectiveness or to reduce the amount of essential oil necessary. This patent uses acacia gum as an emulsifier to form emulsions of essential oils in water.

However, the use of essential oils as a preservative activator is not simple, and requires solutions to be provided to several technical problems.

Indeed, essential oils are natural water-insoluble extracts, known since antiquity for their antiseptic activities, but also for their allergenic potential, which requires finding, for their cosmetic use, a dose balanced between the need to increase this dose, to increase antiseptic activity, and the need to reduce this dose, in order not to trigger allergies. In addition, it is generally desirable for the antiseptic activity to have as broad a spectrum as possible, in order to be able to inhibit growth or kill all microorganisms, namely bacteria, fungi, yeasts, and viruses. The search for a balanced dose and a broad spectrum of activity often leads to using a cocktail of essential oils at very low doses, or to combine some essential oils with other antimicrobial active agents or with compounds potentiating or acting in synergy with essential oils. This takes the approach of complicating the antimicrobial composition, and increasing the risks of harmful interactions.

In addition, modern cosmetics poses an additional problem for the use of essential oils, namely the need to make them active in cosmetic formulations comprising an aqueous phase, and a multitude of ingredients capable of negatively interacting with the essential oil. To exert its antimicrobial activity in the aqueous phase, the essential oil should be dispersed finely or solubilized in this aqueous phase. This dispersion or this solubilization are generally done, at a minimum, by adding a solubilizing surfactant, and more advantageously, by adding a water-soluble organic solvent to the formulation of the cosmetic product as well. All categories of solubilizing surfactants have been envisaged by the prior art.

However, although combinations of solubilizing surfactants and essential oils have been able to show their antimicrobial efficacy, the incorporation of such combinations into cosmetic formulations has shown the potential to destabilize the formulations and in particular cause phase shifts or the formation of solid particles.

Furthermore, the composition of a cosmetic product is very different from that of an in vitro test culture medium. In a cosmetic product, interactions between the constituents of the antimicrobial composition and the ingredients of the cosmetic product may occur, resulting in the alteration or suppression of the antimicrobial activity. It may then prove necessary to increase the dose in the antimicrobial composition to regain the antimicrobial activity in-situ.

Technical Problem

Thus, it is necessary to find a preservative activator composed of natural products or products of natural, biodegradable origin, devoid of transparent or silicone compounds, which is transparent and can be integrated into a cosmetic product without altering the physical/chemical properties of the product, that is without altering or destabilizing the cosmetic product, nor causing phase shifts or the formation of solid particles, for the majority of galenical forms. It is also necessary to develop a formulation which preserves the antimicrobial properties of the activator.

BRIEF DESCRIPTION OF THE DRAWINGS

Other features, details and advantages of the invention will appear from reading the following detailed description, and by analyzing the appended drawings, in which.

SUMMARY OF THE INVENTION

Figure 1:
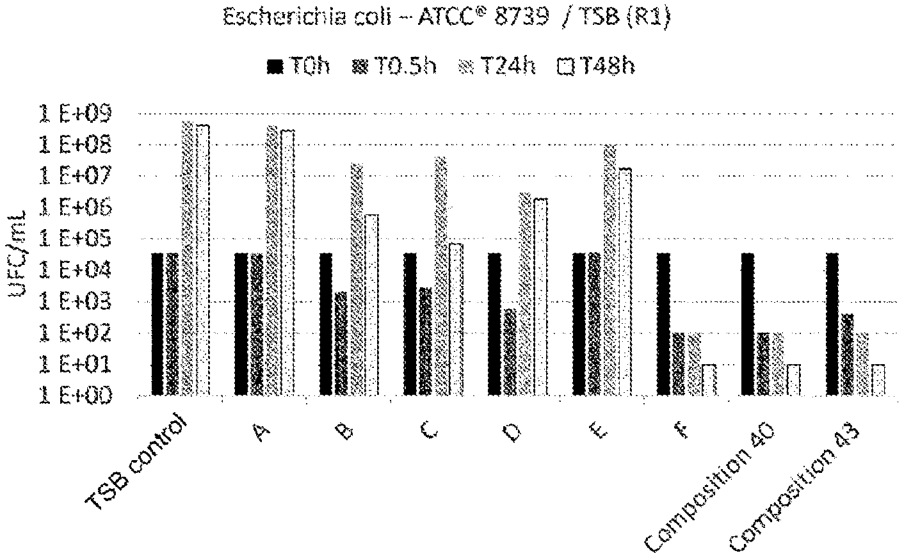
FIG. 1 shows the results of the antimicrobial activity tests of the antimicrobial liquid composition on *Escherichia coli* ATCC® 8739.
Figure 2:
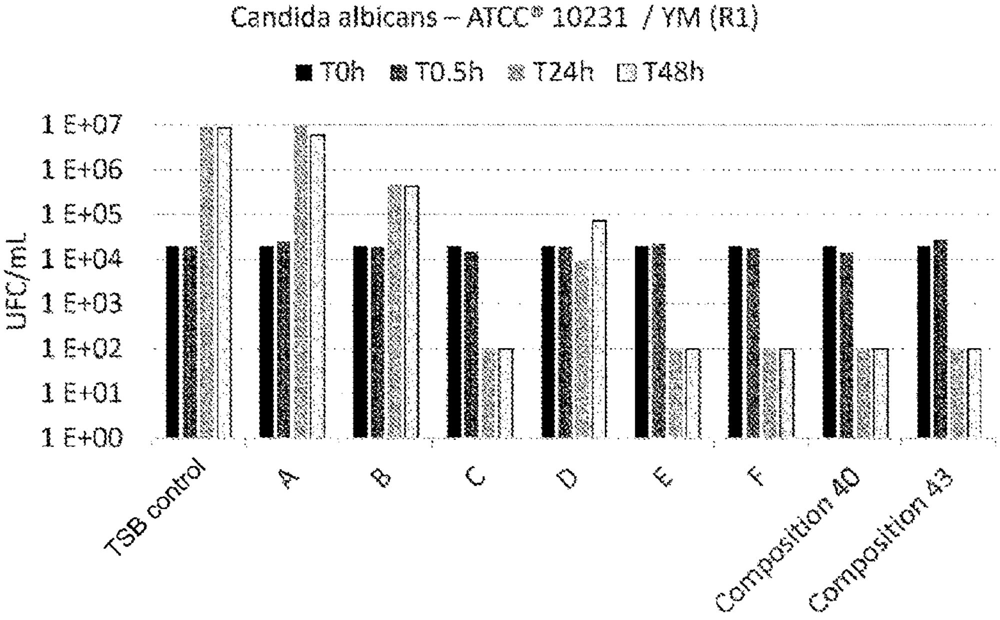
FIG. 2 shows the results of the antimicrobial activity tests of the antimicrobial liquid composition on *Candida albicans* ATCC® 10231.
Figure 3:
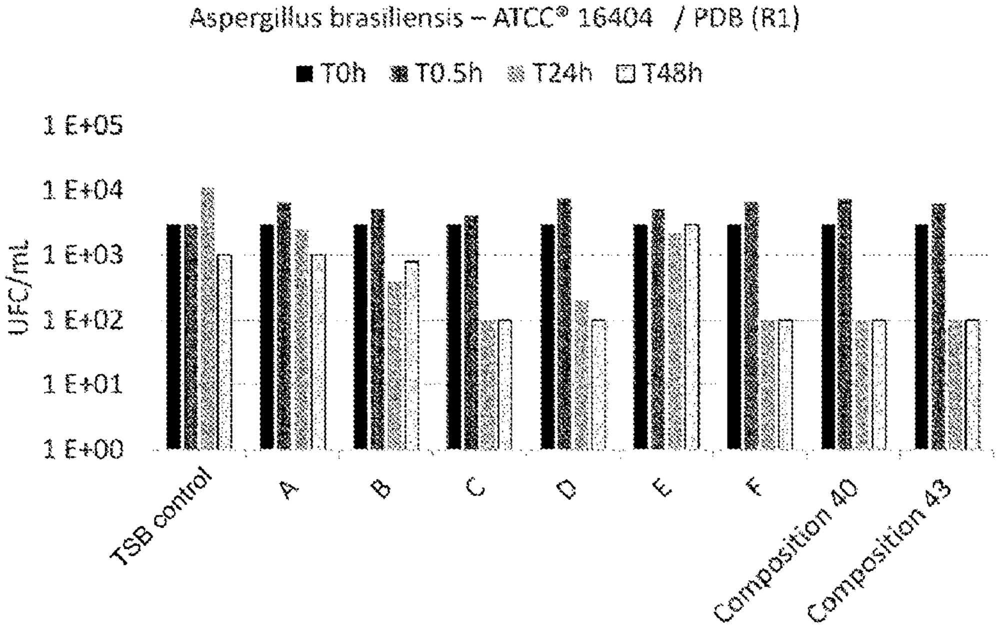
FIG. 3 shows the results of the antimicrobial activity tests of the antimicrobial liquid composition on *Aspergillus brasiliensis* ATCC® 16404.
Figure 4:
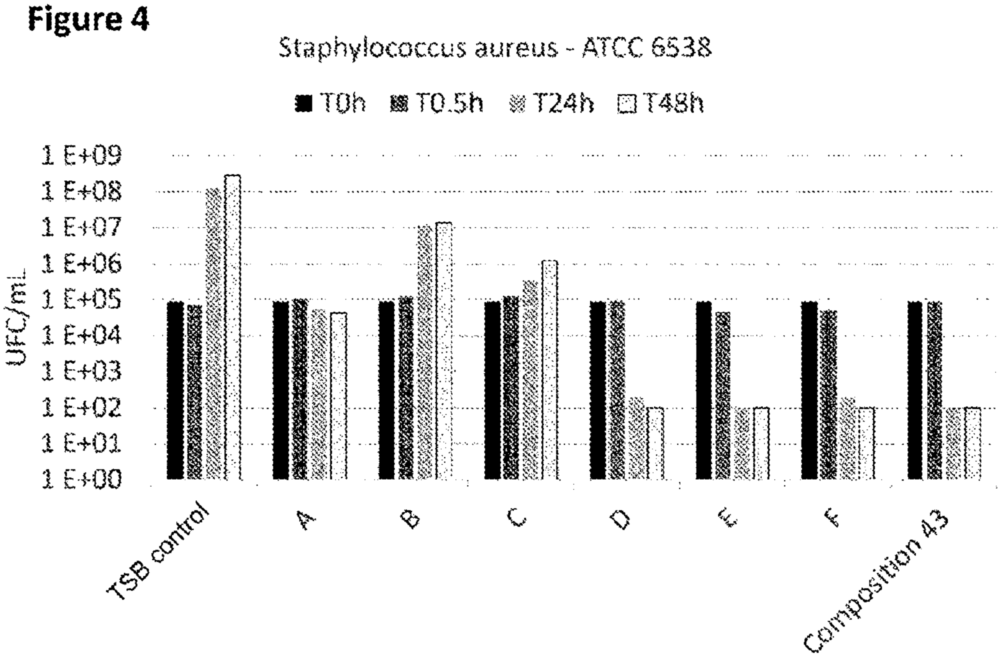
FIG. 4 shows the results of the antimicrobial activity tests of the antimicrobial liquid composition on *Staphylococcus aureus* ATCC® 6538.
Figure 5:
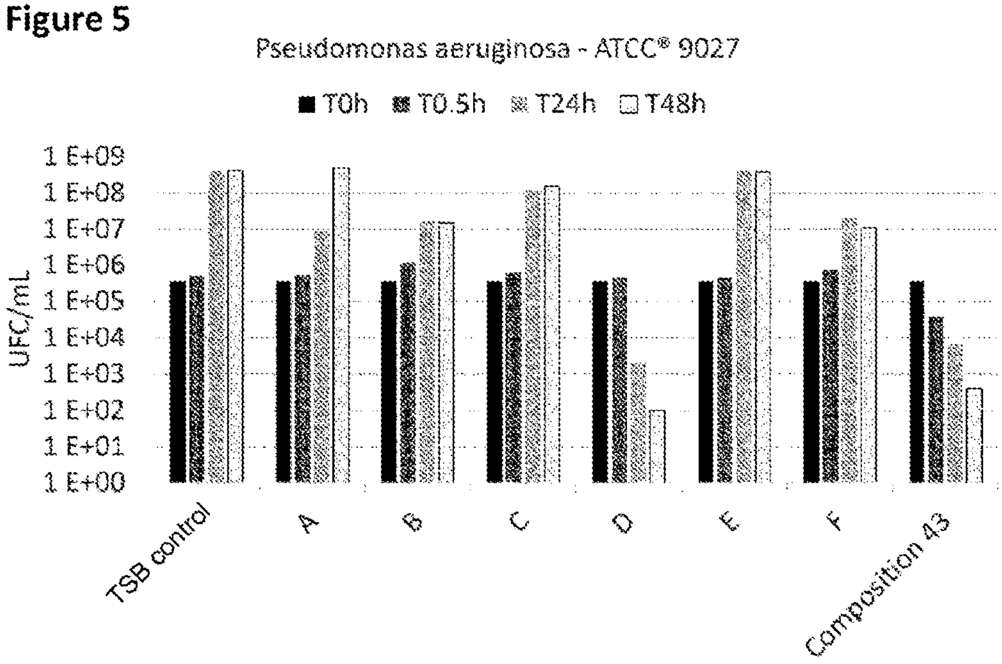
FIG. 5 shows the results of the antimicrobial activity tests of the antimicrobial liquid composition on *Pseudomonas aeruginosa* ATCC® 9027.

The Applicant has demonstrated that antimicrobial compositions according to the invention make it possible to activate preservatives and to increase their antimicrobial protection. Indeed, high logarithmic reductions in the number of colony-forming units of *Pseudomonas aeruginosa, Escherichia coli, Aspergillus brasiliensis, Candida albicans* and *Staphylococcus aureus* are measured when the antimicrobial compositions are introduced into the cosmetic composition, in combination with a preservative, in comparison with a cosmetic composition comprising only a preservative as is usually used.

Thus, the present invention relates to the use of an antimicrobial liquid composition for activating cosmetic product preservatives, said antimicrobial liquid composition comprising:

At least one essential oil chosen from essential oils of species of the genus *Cymbopogon*, essential oils of clove, Bourbon geranium, bay leaf, *Litsea citrata*, lemon balm, chili pepper, West India bay, oregano, tea tree, thyme, lemongrass;

At least one nonionic surfactant chosen from alkyl(poly) glycosides, alkyl glycosides, esters of plant oils, non-ethoxylated polyol fatty esters, C8-C10 alkylglycoside heteropolymers and sorbitan fatty esters, or mixtures thereof, At least one carboxylic acid in free form.

The present invention also relates to antimicrobial compositions comprising essential oil of one of the species of the genus *Cymbopogon,* caprylyl/capryl glucoside, gluconic acid, sodium gluconate, water.

These compositions advantageously make it possible to stabilize the cosmetic products wherein they are incorporated, without altering or destabilizing the cosmetic product, nor causing phase shift or formation of solid particles. Advantageously again, the antimicrobial compositions according to the invention retain their antimicrobial activity once formulated in a cosmetic product.

Thus, the present invention also relates to cosmetic products comprising antimicrobial compositions according to the invention and at least one preservative.

DESCRIPTION OF THE EMBODIMENTS

For purposes of clarity, in the present application:

- the expression "being composed of" will have the same meaning as the expression "comprising", namely to define an open composition.
- constituents other than water, in the antimicrobial composition to which the present application relates, are sometimes sold in the form of aqueous solutions, composed of water and one of said constituents. In order to release this water content, which may vary depending on the constituents and their suppliers, the mass percentages of said constituents other than water in the antimicrobial composition, expressed in % by dry weight, are the mass percentages of the dry masses of said constituents, in other words the mass percentages of said dry constituents, the water being excluded.
- the antimicrobial liquid composition to which the present application relates is an aqueous composition. The amounts of antimicrobial liquid composition used are expressed as raw mass percentages, noted as % by gross weight, making the liquid composition antimicrobial in its entirety, in other words taking into account all its constituents, water included.

The present invention relates to the use of an antimicrobial liquid composition for activating cosmetic product preservatives, said antimicrobial liquid composition comprising:

- At least one essential oil chosen from essential oils of species of the genus *Cymbopogon*, essential oils of clove, Bourbon geranium, bay leaf, *Litsea citrata*, lemon balm, chili pepper, West India bay, oregano, tea tree, thyme, lemongrass, or a mixture of these oils;
- At least one nonionic surfactant chosen from alkyl(poly) glycosides, alkyl glycosides, esters of plant oils, non-ethoxylated polyol fatty esters, C8-C10 alkylglycoside heteropolymers and sorbitan fatty esters, or mixtures thereof,
- At least one carboxylic acid in free form.

According to another embodiment, the present invention relates to the use of an antimicrobial liquid composition for activating cosmetic product preservatives, said antimicrobial liquid composition comprising:

- At least one essential oil chosen from essential oils of species of the genus *Cymbopogon*, essential oils of clove, Bourbon geranium, bay leaf, *Litsea citrata*, lemon balm, chili pepper, West India bay, oregano, tea tree, thyme, lemongrass, or a mixture of these oils;
- At least one nonionic surfactant chosen from alkyl(poly) glycosides,
- At least one carboxylic acid in free form.

Antimicrobial Activity

Within the meaning of the invention, an antimicrobial composition is a composition which has antimicrobial activity, that is to say that the composition is able to slow down the growth of at least some bacteria, fungi or yeasts, better still to inhibit the growth and to lower the numerical population of at least some of them by preventing them from developing and multiplying, and better still to make their presence undetectable and to make them completely disappear by killing them. Consequently, the definition encompasses a slowing down of growth, an inhibition of growth under the known terms of bacteriostatic and fungistatic, and also a lethal activity, called a bactericidal or fungicidal activity.

Cosmetic Product Preservative Activator

When implemented with mass percentages of less than 5% by gross weight, or even 2.5% by weight, with respect to the total weight of the cosmetic product, the antimicrobial composition according to the invention proves to be itself insufficiently effective to preserve a cosmetic product (that is it does not significantly reduce or inhibit growth of bacteria or fungi and does not have a bactericidal or fungicidal activity).

Advantageously, when associated with a usual preservative, the antimicrobial composition according to the invention combines its antimicrobial activity with the activity of said preservative, and potentiates the activity of said preservative. It will then be possible to use a reduced dose of preservative, in association with a suitable dose of antimicrobial composition, to achieve a reduction in the load of microorganisms in the cosmetic product, that is reducing the number of colony-forming units, or even preferably to stabilize the microbiology of the cosmetic product according to the ISO 11930:2019 standard. The antimicrobial composition thus effectively makes it possible to reduce the amount of preservative necessary to retain the cosmetic product, over durations equivalent to the usual preservatives employed at recommended doses, which are generally equal to the maximum concentrations allowed in ready-to-use cosmetic products. The preservatives in cosmetic products are present in the cosmetic composition, either alone or in combination, in a content of about 1% by weight, relative to the total weight of the composition. As demonstrated in the examples, the antimicrobial compositions according to the invention make it possible to reduce the content of preservative (for example 0.4% for potassium sorbate and sodium benzoate), and to use only one preservative.

Thus, a preservative activator is a compound which has insufficient antimicrobial activity in itself in the cosmetic product, but which is capable of increasing the antimicrobial activity of a preservative in the cosmetic product. "Insufficient antimicrobial activity" is understood to mean a compound which does not significantly reduce the growth of bacteria, fungi or yeasts, much less inhibit their growth or kill them. The preservative activator cannot therefore microbiologically stabilize a medium by itself, and therefore cannot be qualified as a preservative within the regulatory definition.

The combination of a preservative with a preservative activator therefore makes it possible to at least increase the antimicrobial activity of the preservative and preferably microbiologically stabilizing a cosmetic product. It is generally sought that this stabilization or increase occurs at a dose of a preservative lower than the dose required when the preservative is used alone.

The antimicrobial activity can be evaluated according to any method known to a skilled person.

The classification can be done by monitoring the reduction in the number of colony-forming units (denoted CFU/mL) seven, fourteen and twenty-eight days after the cosmetic product has been inoculated with a microorganism. The reduction in the number of colony-forming units is expressed as a base-10 logarithm, for example a reduction log corresponds to a reduction of 10^1, that is 10, CFU/mL, or two reduction logs corresponding to a reduction of 10^2, that is 100, CFU/mL.

Preferably, the antimicrobial activity is evaluated according to the international standard ISO 11930:2019 entitled "ISO11930 Cosmetics—Microbiology—Evaluation of the antimicrobial protection of a cosmetic product" which specifies a procedure for the interpretation of the data resulting from the efficacy test of the antimicrobial protection and/or the assessment of microbiological risk during the overall evaluation of the antimicrobial protection of a cosmetic product. This standard makes it possible in particular to classify the microbiological protection level of a cosmetic product against the main pathogens, namely *Escherichia coli, Staphylococcus aureus, Pseudomonas aeruginosa*, and fungi, namely *Candida albicans* and *Aspergillus brasiliensis*.

According to one embodiment, a composition will be considered a preservative activator when, combined with the preservative, it makes it possible to increase by at least 1 log the reduction in the number of colony-forming units of microorganisms present in the medium, preferably at least two logs, preferentially at least 3 logs, compared to the number of colony-forming units when the preservative alone is used.

According to one embodiment, a composition will be considered a preservative activator when, combined with the preservative, it makes it possible to increase by at least 1 log the reduction in the number of colony-forming units of microorganisms present in the medium, preferably at least two logs, preferentially at least 3 logs, compared to the number of colony-forming units of microorganisms when the preservative alone is used, over a period of at least 7 days, preferably 14 days and even preferentially over a period of at least 28 days.

The antimicrobial liquid composition to which the present application relates may be described as a liquid composition with a preservative activator effect since it satisfies the previous definition of a preservative activator. Preferably, the antimicrobial liquid composition is therefore a liquid composition with a preservative activator effect.

According to one embodiment, the antimicrobial composition according to the invention makes it possible to activate a preservative and, combined with said preservative, to reduce by at least one log, preferentially at least two logs, preferentially at least three logs, the number of colony-forming units of *Pseudomonas aeruginosa, Escherichia coli, Aspergillus brasiliensis, Candida albicans* and *Staphylococcus aureus*.

According to one embodiment, the antimicrobial composition according to the invention makes it possible to activate a preservative and, combined with said preservative, to reduce by at least one log, preferentially by at least two logs, preferentially at least 3 logs, the number of colony-forming units of *Pseudomonas aeruginosa, Escherichia coli, Aspergillus brasiliensis, Candida albicans* and *Staphylococcus aureus* over a period of at least 7 days, preferably 14 days and even preferentially over a period of at least 28 days.

Essential Oil

According to one embodiment, the antimicrobial composition comprises at least one essential oil chosen from essential oils of species of the genus *Cymbopogon*, essential oils of clove, Bourbon geranium, bay leaf, *Litsea citrata*, lemon balm, chili pepper, West India bay, oregano, tea tree, thyme, lemongrass, or a mixture of these oils.

According to one embodiment, the essential oil is chosen from essential oils of species of the genus *Cymbopogon*.

*Cymbopogon* is a genus of monocotyledonous plants of the Poaceae family, panicicidae subfamily, which comprises about fifty species originating from tropical and subtropical regions of Africa, Asia and Australia. These are herbaceous plants, generally perennial, rarely annual, caespitose or rhizomatous, the stems of which (thatch) can reach 15 to 300 cm long.

The essential oil of species of the genus *Cymbopogon* is selected from the oils of species of the genus *Cymbopogon*, rich in citral, neral, geraniol and geraniol. Preferably, the essential oil of the genus *Cymbopogon* is chosen from essential oils of species of species of the genus *Cymbopogon* having approximately 30% by weight in neral, approximately 40% by weight in geraniol, and 5% by weight in geraniol. These mass percentages are usually determined by chromatography.

Essential oils of species of the genus *Cymppogon* include:

*Cymbopogon citratus* (DC.) Stapf., also referred to as West Indian lemongrass or India citronella or India *verbena*

*Cymbopogon flexuosus* Stapf., also called Fast indian lemongrass,

*Cymbopogon nardus*, also called Ceylon citronella or Sri Lanka citronella,

*Cymbopogon nardus* (L.) Watson, *Cymbopogon nardus* (L.) Rendel,

*Cymbopogon schoenanthus* (L.), also called Camel grass or geranium grass,

*Cymbopogon winterianus* Jowitt, also called Java citronella

*Cymbopogon martinii* var. *sofia*, also called gingergrass, and *Cymbopogon martinii* var. *motia, Cymbogopon maartinii* roxb., also called palmarosa.

According to one embodiment, the essential oil of *Cymbopogon* is chosen from essential oils of the species *Cymbopogon flexuosus* Stapf. and *Cymbopogon citratus* (DC.) Stapf. Most preferentially, the essential oil is an essential oil of citronella of the species *Cymbopogon citratus* (DC.) Stapf. Typically, essential oils of species *Cymbopogon flexuosus* Stapf. and *Cymbopogon citratus* (DC.) Stapf. about 30% by weight in neral, about 40% by weight in geranial, and 5% by weight in geraniol Examples of essential oils of species of the genus *Cymbopogon* useful to the antimicrobial liquid composition to which the present application relates, mention may be made of those sold under the names *Cymbopogon flexuosus* Oil® by Elixens, and HE Lemongrass citratus of Sri-Lankan origin by H. Reynaud & Fils.

Essential oils of oregano include compact inflorescences, Greek oregano, compact oregano, green oregano, and Spanish oregano.

Essential oils of thyme oils include the essential oils of wild thyme, thyme with borneol, thyme with carvacrol, thyme with linalol, thyme with thujanol, thyme with thymol, The essential oil may also be chosen advantageously from other oils rich in citral, in neral, in geranial and geraniol.

It may be, for example, essential oil of *Litsea citrata* which contains approximately 40% by weight of geranial and approximately 30% by weight of neral or essential lemon oil of the species *Melissa officinalis*, relative to the total weight of essential oil.

It may also be an essential oil rich in geranial and geraniol such as in particular essential oil of palmarosa (*Cymbopogon martini*) which ordinarily contains 80% to 85% by weight of geraniol relative to the total weight of essential oil.

According to one embodiment, the essential oil will comprise at least one active molecule chosen from active molecules which make up the essential oil of lemongrass species *Cymbopogon flexuosus* and *Cymbopogon citratus*: The trans isomer of citral, known under the name geranial or citral A, with IUPAC name (E)-3,7-dimethylocta-2,6-dienal; the cis isomer of citral, known under the name of neral, or citral B, with IUPAC name (Z)-3,7-dimethylocta-2,6-dienal; geraniol, with IUPAC name (2E)-3,7-dimethylocta-2,6-dien-1-ol.

Thus, according to one embodiment, the essential oil is chosen from essential oils of *Cymbopogon, Litsea citrata*, or lemon balm.

According to another embodiment, the essential oil useful for the antimicrobial composition to which the present application relates may be selected from the essential oils of ajowan (also called Indian thyme), star anise (also called badiane), basil, China or Ceylon cinnamon, cardamom, Provence cypress, lemon-scented gum, Tasmanian blue gum, *Eucalyptus radiata*, black spruce, tarragon, fennel, wintergreen, juniper, geranium grass, rose geranium, geranium bourbon, gingergrass, clove, fragrant inula, noble laurel, lavandin reydovan, fine lavender, spike lavender, true lavender, lavandin, lavandin super, garden marjoram, shell marjoram, *melaleuca*, field mint, peppermint, lemon balm, red myrtle, neroli, niaouli, petitgrain bigarade, Scots pine, ravintsara (also known as ravintsare or Madagascar camphor), rosemary cineole, rosemary camphor, rosemary *officinalis*, saro, garden savory, mountain savory, lemongrass, wild thyme, exotic *verbena*, Indian *verbena*, or a blend of these oils.

The essential oil may also be an oil rich in phenols, in particular in carvacrol (present for example in the essential oil of savory), in thymol (present for example in the essential oil of thyme with thymol) and of eugenol (present for example in the essential oil of clove). These phenols are responsible for the fungicidal and bactericidal activities of the essential oils which contain them. Mention may more particularly be made, as phenol-rich oils, of the essential oils of thyme (*Thymus mastichina, Thymus vulgaris, Thymus zygis, Thymus thymi*), of chili pepper (*Pimenta racemosa, Pimenta acris*), of ajowan (*Trachyspermum ammi*), of clove (*Eugenia caryophylllus*), of mountain savory (*Satureja montana*), of oregano (*Origanum heracleoticum* (Greek oregano)), *Origanum majorana, Origanum vulgare, Origanum compactum* (compact oregano), Spanish oregano (*Corydothymus capitatus*), Ceylon cinnamon (*Cinnamomum verum*).

According to one embodiment, the essential oil comprises at least one active molecule chosen from monoterpenols, which are alcohols with 10 carbon atoms, preferably geraniol, linalool, thujanol, myrcenol, terpineol, menthol and piperitol. The essential oils which comprise these active molecules are essential oils of palmarosa *Cymbopogon martinii*, spike lavender *Lavandula spica* peppermint *Mentha piperita*, organic marjoram *Origanum majorana* and tea tree of the species *Melaleuca alternifolia.*

According to one embodiment, another essential oil lean in at least one phenol, monoterpenol, terpene oxide, aromatic aldehyde, terpene aldehyde, phenylpropene, monoterpene hydrocarbon, and sesquiterpene hydrocarbon, can be added to the composition to which the present application relates, for example to flavor it, change its odor or act on its antimicrobial activity. It may be chosen from essential oil of cedar, soft orange essential oil, lemon essential oil, green or red mandarin essential oil, or essential oil of wintergreen.

The total amount of essential oils present in the antimicrobial liquid composition can range from 0.1% to 10% by dry weight, preferably from 0.5% to 7% by dry weight, more preferably from 1% to 5% by dry weight, and most preferentially from 1.5% to 3% by dry weight, relative to the total weight of the antimicrobial liquid composition.

The ratio of the total dry mass of nonionic surfactants to the total dry mass of essential oils can also be greater than or equal to 2, preferentially greater than or equal to 3, more preferably greater than or equal to 4, and most preferentially greater than or equal to 5. The essential oil or oils are advantageously present in the antimicrobial composition in an amount that is lower than the amount of nonionic surfactants. The selection of being lower makes it possible to best solubilize the essential oil(s) in the water of the antimicrobial liquid composition, and also contributes to maintaining this solubilization in water of the cosmetic product when said antimicrobial liquid composition is diluted in said cosmetic product, and in particular in the water of said cosmetic product.

This ratio advantageously makes it possible to obtain a stable antimicrobial liquid composition, without phase shift or precipitation over time, while being transparent or opalescent, in the concentrated state or even after high dilution in water.

Nonionic Surfactants

According to one embodiment, the nonionic surfactant is chosen from:

- alcohols, alpha-diols and alkyl(C1-C20)phenols, these compounds being polyethoxylated and/or polypropoxylated and/or polyglycerolated, the number of ethylene oxide and/or propylene oxide groups being able to range from 1 to 100, and the number of glycerol groups possibly ranging from 2 to 30; or else these compounds comprising at least one fatty chain comprising from 8 to 40 carbon atoms, in particular from 16 to 30 carbon atoms; in particular, alcohols comprising at least one saturated or non-linear or branched, oxyethylenated, C8-C40 alkyl chain comprising from 1 to 100 mol of ethylene oxide, preferably from 2 to 50, more particularly from 2 to 40 mol of ethylene oxide and comprising one or two fatty chains;
- ethylene oxide and propylene oxide condensates on fatty alcohols;
- polyethoxylated fatty amides preferably having from 2 to 30 ethylene oxide units, polyglycerolated fatty amides comprising, on average from 1 to 5 glycerol groups and in particular from 1.5 to 4;
- ethoxylated sorbitan fatty acid esters preferably having from 2 to 40 ethylene oxide units;
- fatty acid esters;
- polyoxyalkylenated fatty acid esters, preferably polyoxyethylenated, having from 2 to 150 moles of ethylene oxide, including oxyethylenated vegetable oils;
- N-(alkyl en C6-C24)glucamine derivatives,
- amine oxides such as (C10-C14 alkyl)amine oxides or N—(C10-C14 acyl)-aminopropylmorpholine;
- non-ethoxylated polyol fatty esters, and particularly from non-ethoxylated fatty esters of glycerol, polyglycerols, sorbitol, sorbitan, anhydrohexitols, such as in particular isosorbide, mannitol, xylitol, erythritol, maltitol, sucrose, glucose, polydextrose, hydrogenated glucose syrups, dextrins and hydrolyzed starches.
- polyglycerol and saturated or unsaturated C4-C20, preferably C8-C18, and more preferably C18 esters, for example polyglyceryl-2 dipolyhydroxystearate and polyglyceryl-3 diisostearate,
- esters of plant oils, in particular of coconut oil esters, for example coco-caprylate,
- and mixtures thereof.

According to another embodiment, the nonionic surfactant is selected from alkyl(poly)glycosides, which are represented by the following general formula:

$$R_1O—(R_2O)_t—(G)_v$$

wherein:

$R_1$ represents a linear or branched alkyl or alkenyl radical comprising 6 to 24 carbon atoms, or 6 to 18 carbon atoms, or 6 to 12 carbon atoms; or an alkylphenyl radical, the linear or branched alkyl radical of which comprises 6 to 24 carbon atoms, or 6 to 18 carbon atoms, or 6 to 12 carbon atoms, $R_2$ represents an alkylene radical comprising 2 to 4 carbon atoms, G represents a sugar unit having 5 to 6 carbon atoms, t denotes a value ranging from 0 to 10, preferably from 0 to 4, v denotes a value ranging from 1 to 15, preferably from 1 to 4, Preferably, the alkyl(poly)glycoside surfactants are compounds of the formula described above wherein:

$R_1$ denotes a saturated or unsaturated, linear or branched alkyl radical comprising 6 to 18 carbon atoms, or 6 to 12 carbon atoms, $R_2$ represents an alkylene radical comprising 2 to 4 carbon atoms, t denotes a value ranging from 0 to 3, preferably equal to 0, G denotes glucose, fructose or galactose, preferably glucose;

the degree of polymerization, that is the value of v, which may range from 1 to 15, preferably from 1 to 4; the average degree of polymerization being more particularly between 1 and 2.

The glucosidic bonds between sugar units are generally of type 1-6 or 1-4, preferably of type 1-4. Preferably, the alkyl(poly)glycoside surfactant is an alkyl(poly)glucoside surfactant, that is an alkyl(poly)glycoside surfactant where G is a glucose. The alkyl C6/C16-(poly)glucosides 1,4, C6/C12-(poly)glucosides 1,4, and in particular and in particular decyl glucosides 1,4, dodecylglucosides, the hetpoglucosides, caprylyl glucosides, capryl glucosides and capryl/capryl glucosides, are most particularly preferred.

According to one embodiment, the surfactant is chosen from capryl/capryl glucosides.

Among the commercial products, mention may be made of the products sold by COGNIS under the names PLANTAREN® (600 CS/U, 1200 and 2000) or PLANTACARE® (818, 1200 and 2000); the products sold by SEPPIC under the names Orax CG 110 and ORAMIX® NS 100; the products sold by BASF under the name LUTENSOL GD 70 or the products sold by CHEM Y under the name AG10 LK.

The nonionic surfactant may also be chosen from alkyl (poly)glycosides, preferentially alkyl(poly)glucosides, with an HLB greater than or equal to 10, or greater than or equal to 12, or greater than or equal to 14.

The alkyl(poly)glycosides, preferentially the alkyl(poly) glycosides, may also be combined with fatty alcohols.

The nonionic surfactant can also be chosen from heteropolymers of C8-C10 alkylglycoside and sorbitan fatty esters, preferentially from heteropolymers of C8-C10 alkylglycosides and sorbitan C4-C20 fatty esters, and more preferably from heteropolymers of C10 alkyl glycosides and sorbitan C18 fatty esters. An example of such a heteropolymer is Poly Suga® Mulse D9 from Colonial Chemical Inc.

The total amount of nonionic surfactants in the antimicrobial liquid composition is greater than or equal to 1% by weight, preferentially greater than or equal to 5% by weight, more preferably greater than or equal to 7.5% by weight, and most preferentially greater than or equal to 10% by weight, relative to the total weight of said antimicrobial liquid composition.

Advantageously, the total amount of nonionic surfactants present in the antimicrobial liquid composition may range from 1% to 50% by weight, preferentially from 1% to 40%, preferentially from 5% to 40% by weight, preferentially from 5% to 30% by weight, more preferably from 7.5% to 30% by weight, more preferably from 7.5% to 20% by weight, and most preferentially from 10% to 20% by weight, relative to the total weight of the antimicrobial liquid composition.

The ratio of the total dry mass of nonionic surfactants to the total dry mass of essential oils can also be greater than or equal to 2, preferentially greater than or equal to 3, more preferably greater than or equal to 4, and most preferentially greater than or equal to 5. The nonionic surfactant(s) are advantageously present in the antimicrobial composition in an amount which is greater than the amount of the essential oil(s). The selection of being greater makes it possible to best solubilize the essential oil(s) in the water of the antimicrobial liquid composition, and also contributes to maintaining this solubilization in water of the cosmetic product when said antimicrobial liquid composition is diluted in said cosmetic product, and in particular in the water of said cosmetic product.

Advantageously, according to the embodiment where the nonionic surfactant is caprylyl/capryl glucoside, a value of the ratio of the weight of caprylyl/capryl glucoside to the mass of essential oil greater than or equal to 2, preferably greater than or equal to 3, more preferably greater than or equal to 4, most preferably greater than or equal to 5, makes it possible to obtain an antimicrobial liquid composition totally transparent and stable over time in the concentrated state and in the state diluted in water. Cosmetic product formulators generally prefer transparent ingredients to formulate their products.

Advantageously, the selection of the nonionic surfactants according to the invention makes the liquid composition antimicrobial compatible with ionic surfactants and zwitterionic surfactants. It is therefore possible to add the antimicrobial composition to a cosmetic product comprising another type of surfactant while keeping good physical stability of the state of the cosmetic product, and keeping the effects of ionic or zwitterionic surfactants, that is without masking or neutralizing the effects of these surfactants.

Thus, the antimicrobial composition according to the invention can be added to shower shampoos or gels, which comprise anionic surfactants, often in a high quantity, while retaining the detergent power of the anionic surfactants, and while retaining the liquid single-phase or gel state. The antimicrobial liquid composition may also be added to a coloring solution or a conditioner, generally comprising cationic surfactants or cationic polymers, while retaining the coloring and hair conditioning capability.

Free Carboxylic Acids

The free carboxylic acid useful for the antimicrobial composition to which the present application relates is chosen from monocarboxylic acids and polycarboxylic acids, linear or branched, preferentially from monocarboxylic acids, dicarboxylic acids, and tricarboxylic acids, most preferably from monocarboxylic acids and dicarboxylic acids.

"Free" means that the carboxylic acid function is either in its protonated form COOH, or in its ionized form COO— associated with a counterion H or H3O, in proportions depending on the pH value of the aqueous solution of acid and on the strength of the acid characterized by its pKa.

According to one embodiment, the carboxylic acid is chosen from monocarboxylic acids, the carbon chain of which consists of 2 to 12 carbon atoms, or 3 to 8 carbon atoms. Mention may be made of gluconic acid (pKa=3.86), lactic acid, glycolic acid, glucuronic acid, maltobionic acid, lactobionic acid, malic acid, tartaric acid, mandelic acid, fatty acids (or aliphatic chain carboxylic acids) having a carbon chain of 4 to 12 atoms, preferably natural fatty acids such as, in particular, propionic acid, butyric acid, caproic acid, caprylic acid, capric and lauric acids. According to a variant of this embodiment, the carboxylic acid is chosen from gluconic acid, glucuronic acid, maltobionic acid, preferably the carboxylic acid is gluconic acid. According to a variant of this embodiment, the monocarboxylic acid is the cyclic form of gluconic acid, called gluconolactone.

According to another embodiment, the carboxylic acid is chosen from polycarboxylic acids, and preferably from dicarboxylic acids and tricarboxylic acids, and most preferentially from aspartic acid, adipic acid, malonic acid, pimelic acid, succinic acid, glucaric acid, and glutaric acid, and even more preferably is succinic acid.

The carboxylic acid(s) or polycarboxylic acids useful to the antimicrobial liquid composition to which the present application relates are further characterized by a pKa value ranging from 3 to 6, preferentially from 4 to 6.

The total amount of free carboxylic acids present in the antimicrobial liquid composition can range from 10% to 70% by dry weight, preferentially from 20% to 60% by dry weight, more preferably from 25% to 50% by dry weight, and most preferably from 27.5% to 40% by dry weight, relative to the total weight of the antimicrobial liquid composition.

Carboxylic Acid Salts

The carboxylic acid salt useful for the antimicrobial composition to which the present application relates is chosen from monocarboxylic acid salts or linear or branched polycarboxylic acid salts. In an acid salt, the carboxylic acid function is either in the protonated form COOH, or in the ionized form COO— associated with a metal counterion M, in proportions dependent on the pH value of the aqueous acid solution, the pKa acidity constant of the corresponding free acid, and the dissociation constant of the pKd salt.

The carboxylic acid salt(s) is or are chosen from sodium, magnesium, zinc, calcium, potassium, iron, lithium, carboxylic acid selected from carboxylic acids of the "free carboxylic acid" portion of the present application.

According to one embodiment, the carboxylic acid salt is a salt of the free carboxylic acid useful for the composition to which the present application relates. According to a variant of this embodiment, said carboxylic acid is divided into at most 35% by dry weight of the salt of said carboxylic acid and at least 65% by dry weight of said free carboxylic acid. Such a variant is gluconic acid divided into 35% by dry weight of sodium gluconate and 65% by dry weight of free gluconic acid. Advantageously, such a mixture of acid and its salt has a pH better tolerated by the skin and is less irritant than the acid alone can be.

According to one embodiment, the carboxylic acid salt(s) is or are chosen from sodium, magnesium, zinc, calcium, potassium, iron or lithium salts of gluconic acid or succinic acid, and preferably the carboxylic acid salt(s) are chosen from sodium gluconate and sodium succinate, and most preferably the carboxylic acid salt is sodium gluconate.

The total amount of carboxylic acid salts present in the antimicrobial liquid composition can range from 1% to 50% by dry weight, preferably from 5% to 30% by dry weight, more preferably from 10% to 20% by dry weight, and most preferentially from 15% to 17.5% by dry weight, relative to the total weight of the antimicrobial liquid composition.

Water

The water present in the antimicrobial liquid composition may be decarbonated water, or demineralized water.

The amount of water present in the antimicrobial liquid composition may range from 20% to 75% by weight, preferably from 30% to 65% by weight, more preferably from 35% to 55% by weight, relative to the total weight of the antimicrobial liquid composition.

PH of the Antimicrobial Liquid Composition:

The pH of the antimicrobial liquid composition to which the present application relates may range from 2 to 9, preferentially from 3 to 8, more preferably from 4 to 7, and even more preferably from 4.5 to 6.5, and even more preferably from 5.5 to 6.2.

Preservatives

For the usual preservatives in question and their dosages depending on the precise applications, refer to the list of French Cosmetics Regulation no. 1223/2009 in appendix 5 entitled "liste des agents conservateurs admis dans les produits cosmetiques" (list of preservatives allowed in cosmetic products).

Thus, the preservative can be chosen from propionic acid, calcium propionate, formaldehyde, paraformaldehyde, o-phenylphenol or salts thereof, zinc pyrithione, sodium sulfites, bisulfites or metabisulfites, ammonium, potassium, chlorobutanol, methylparaben, ethylparaben, propylparaben, formic acid and salts thereof such as sodium formate, benzoic acid and salts thereof such as sodium benzoate, sorbic acid and salts thereof such as calcium sorbate, sodium sorbate, potassium sorbate, salicylic acid and salts thereof, dehydroacetic acid and salts thereof such as sodium dehydroacetate, undecylenic acid and salts thereof, such as calcium undecylenate, potassium undecylenate, sodium undecylenate, phenoxyethanol, 1,2-Dimethylol-5,6-dimethylhydantoine, benzyl alcohol, chlorhexidine, chlorhexidine diacetate, chlorhexidine digluconate, chlorhexidine dihydrochloride, behentrimonium chloride, cetrimonium chloride, cetrimonium bromide, laurtrimonium chloride, laurtrimonium bromide, steartrimonium chloride, steartrimonium bromide, hexamidine, hexamidine diisethionate, chlorphenesin, benzalkonium chloride, benzalkonium bromide, benzalkonium saccharinate, ethyl lauroyl arginate.

According to one embodiment, the antimicrobial composition is a preservative activator for the following preservatives: benzoic acid, sodium benzoate, salicylic acid and salts thereof, sorbic acid, calcium sorbate, sodium sorbate, potassium sorbate, dehydroacetic acid, sodium dehydroacetate, undecylenic acid, calcium undecylenate, potassium undecylenate, sodium undecylenate, phenoxyethanol, 1,2-Dimethylol-5,6-dimethylhydantoine, benzyl alcohol, chlorhexidine, chlorhexidine diacetate, chlorhexidine digluconate, chlorhexidine dihydrochloride, behentrimonium chloride, cetrimonium chloride, cetrimonium bromide, laurtrimonium chloride, laurtrimonium bromide, steartrimonium chloride, steartrimonium bromide, hexamidine, hexamidine diisethionate, chlorphenesin, benzalkonium chloride, benzalkonium bromide, benzalkonium saccharinate, ethyl lauroyl arginate.

According to one embodiment, the preservative is chosen from formic acid and salts thereof, dehydroacetic acid and salts thereof, benzoic acid and salts thereof, sorbic acid and salts thereof, phenoxyethanol, benzyl alcohol and salts thereof. More preferably, the preservative activated by the antimicrobial liquid composition is selected from benzoic acid, sorbic acid, phenoxyethanol, benzyl alcohol, sodium benzoate, potassium sorbate. Even more preferably, the preservative is selected from phenoxyethanol, benzyl alcohol, sodium benzoate and potassium sorbate.

According to one embodiment, the preservative activated by the antimicrobial liquid composition is chosen from sorbic acid and salts thereof of calcium, sodium, potassium, magnesium or zinc, or a mixture thereof. Even more preferably, the preservative is selected from sorbic acid, calcium sorbate, sodium sorbate, potassium sorbate. Most preferably, the preservative is potassium sorbate.

According to one embodiment, the antimicrobial composition according to the invention makes it possible to activate the preservative power of phenoxyethanol with respect to *Pseudomonas aeruginosa, Escherichia coli, Staphylococcus aureus* and *Aspergillus brasiliensis.*

According to one embodiment, the antimicrobial composition according to the invention makes it possible to activate phenoxyethanol and, combined with said phenoxyethanol, to reduce by at least two logs the number of colony-forming units of *Pseudomonas aeruginosa*, de *Staphylococcus aureus*, d'*Aspergillus brasiliensis* and *Escherichia coli.*

According to one embodiment, the antimicrobial composition according to the invention makes it possible to activate phenoxyethanol and thus allows a reduction in the number of colony-forming units relative to phenoxyethanol alone, greater than:

- for *Pseudomonas aeruginosa*: at least 2 logs at 7 days, at least 3 logs at 14 days,
- for *Staphylococcus aureus*: at least 3 logs at 7 days, at least 2 logs at 14 days,
- and for *Escherichia coli*: at least 2 logs at 7 days and 14 days, at least 1 log at 28 days, —and for *Aspergillus brasiliensis*: at least 1 log at 14 days and at 28 days.

According to one embodiment, the antimicrobial composition according to the invention makes it possible to activate the preservative power of benzyl alcohol with respect to *Pseudomonas aeruginosa, Staphylococcus aureus*, and *Escherichia coli.*

According to one embodiment, the antimicrobial composition according to the invention makes it possible to activate benzyl alcohol and thus allows a reduction in the number of colony-forming units relative to benzyl alcohol alone, greater than:

- for *Pseudomonas aeruginosa*: at least 3 logs at 7 days, at least 4 logs at 14 days,
- for *Staphylococcus aureus*: at least 3 logs at 7 days, at least 2 logs at 14 days,
- and for *Escherichia coli*: at least 1 log at 7 days, at least 3 logs at 14 days, at least 4 logs at 28 days,
- According to one embodiment, the antimicrobial composition according to the invention makes it possible to activate the preservative power of sodium benzoate with respect to *Pseudomonas aeruginosa, Staphylococcus aureus, Escherichia coli, Aspergillus brasiliensis*, and *Candida albicans.*

According to one embodiment, the antimicrobial composition according to the invention makes it possible to activate sodium benzoate and thus allows a reduction in the number of colony-forming units relative to sodium benzoate alone, greater than:

- for *Pseudomonas aeruginosa*: at least 1 log at 7 days, at least 3 logs at 14 days,
- and for *Staphylococcus aureus*: at least 3 logs at 7 days, at least 1 logs at 14 days,
- and for *Escherichia coli*: at least 3 logs at 14 days,
- and for *Candida albicans*: at least 1 log at 7 days, at least 2 logs at 24 days, at least 3 logs at 28 days,
- and for *Aspergillus brasiliensis*: at least 1 log at 28 days,
- According to one embodiment, the antimicrobial composition according to the invention makes it possible to activate the preservative power of potassium sorbate relative to *Pseudomonas aeruginosa, Staphylococcus aureus, Escherichia coli*, of *Candida albicans* and *Aspergillus brasiliensis.*

According to one embodiment, the antimicrobial composition according to the invention makes it possible to activate potassium sorbate and thus allows a reduction in the number of colony-forming units relative to potassium sorbate alone, greater than:

- for *Pseudomonas aeruginosa*: at least 3 logs at 7 days, at least 5 logs at 14 days and at 28 days,
- and for *Staphylococcus aureus*: at least 2 logs at 7 days,
- and for *Escherichia coli*: at least 3 logs at 7 days, at least 1 log at 14 days,
- for *Pseudomonas aeruginosa*: at least 1 log at 7 days, at least 3 logs at 14 days and at 28 days,
- and for *Aspergillus brasiliensis*: at least 2 logs at 14 days and at 28 days.

The use of an antimicrobial liquid composition to activate a cosmetic product preservative in a cosmetic product may be made with:

- an amount of antimicrobial liquid composition which may range from at least 0.1% by gross weight, preferably at least 0.5% by gross weight, more preferably at least 0.75% by gross weight, preferably at least 1% by gross weight, and even more preferably at least 1.5% by gross weight,
- and a quantity of preservative which may be up to 2.5% by gross weight, preferably up to 1.5% by gross weight, more preferably up to 1% by gross weight, preferably up to 0.7% by gross weight, and even more preferably up to 0.6% by gross weight, relative to the total weight of the cosmetic product.

The use of an antimicrobial liquid composition to activate a cosmetic product preservative in a cosmetic product may be made with:

- an amount of antimicrobial liquid composition which may range from 0.1% to 5% by gross weight, preferably from 0.5% to 3% by gross weight, more preferably from 0.75% to 2% by gross weight, and most preferably from 1% to 1.5% by gross weight of said at least one antimicrobial liquid composition,
- and a usual amount of preservative, which may range from 0.1% to 2.5% by gross weight, preferably from 0.2% to 1.5% by gross weight, more preferably from 0.3% to 1% by gross weight, and most preferentially from 0.4% to 0.7% by gross weight, relative to the total weight of the cosmetic product.

Depending on the nature of the preservative used, the antimicrobial composition makes it possible to reduce by at least 35%, or even at least 50%, indeed even better still at least 60%, the amount of usual preservative used in cosmetic formulations. Thus, it is generally possible to use them only at very low levels not exceeding 0.5% by weight, or even 0.4% by gross weight, relative to the total weight of the cosmetic product. Microbiological stability may be equal to or even better than with the usual preservative used alone and at the recommended dose.

Antimicrobial Compositions

According to one embodiment, the antimicrobial composition to which the present application relates comprises, or consists of:

- an essential oil consisting of citral and geraniol, preferentially a lemongrass oil consisting of citral and geraniol,
- an alkyl-bearing alkyl glucoside having from 6 to 12 carbon atoms, preferentially of caprylyl/capryl glucoside,
- a carboxylic acid, preferably gluconic acid or succinic acid, most preferably gluconic acid,
- a carboxylic acid salt, preferably sodium gluconate or sodium succinate, most preferentially sodium gluconate,
- water.

According to one embodiment, the antimicrobial composition comprises, or consists of:

- an essential oil, preferably lemongrass comprising at least 50% by weight of citral and geraniol relative to the weight of said essential oil, in a percentage by weight of 0.1% to 10% by dry weight, preferably from 0.5% to 7% by dry weight, more preferably from 1% to 5% by dry weight, and most preferentially from 1.5% to 3% by dry weight,
- from 1% to 40% by dry weight of a fatty chain-bearing alkylglucoside having 6 to 12 carbon atoms, preferably caprylyl/capryl glucoside, preferably from 5% to 30% by dry weight, more preferably from 7.5% to 20% by dry weight,
- from 10% to 70% by dry weight of gluconic acid, succinic acid, sodium gluconate or sodium succinate, preferably from 20% to 60% by dry weight, more preferably from 25% to 50% by dry weight, and most preferably from 27.5% to 40% by dry weight,
- and water, the percentages by weight being expressed in relation to the total weight of said antimicrobial composition.

Embodiments with terpene aldehydes and without benzene aldehydes have the advantage of being considered generally less irritating and less allergenic for the skin than embodiments with benzene aldehydes.

According to one embodiment, the present invention relates to an antimicrobial liquid composition comprising, preferably consisting of:

- an essential oil selected from essential oils of clove, citronella, geranium bourbon, geranium grass, lemongrass, lemongrass, West India lemongrass, East India lemongrass, *Litsea citrata*, lemon balm, palmarosa, chili pepper, West India bay, oregano, tea tree, thyme, lemongrass,
- a nonionic surfactant chosen from alkyl(poly)glycosides, preferably from alkyl(poly)glucosides,
- a free carboxylic acid selected from gluconic acid, succinic acid,
- water.

According to one embodiment, the antimicrobial liquid composition comprises, preferably consists of:

- an essential oil chosen from essential citronella oils, and essential oils of West India lemongrass, East India lemongrass, and preferentially from essential oils of species of the genus *Cymbopogon,*
- a nonionic surfactant chosen from alkyl(poly)glycosides, preferably from alkyl(poly)glucosides,
- a free carboxylic acid selected from gluconic acid, succinic acid,
- water.

According to one embodiment, the antimicrobial liquid composition comprises, preferably consists of:

- essential oil of one of the species of the genus *Cymbopogon,*
- caprylyl/capryl glucoside,
- gluconic acid,
- water.

According to one embodiment, the antimicrobial liquid composition comprises:

- essential oil of one of the species of the genus *Cymbopogon* present in a mass percentage ranging from 0.1% to 10% by dry weight, preferably from 0.5% to 7% by dry weight, more preferably from 1% to 5% by dry weight, and most preferentially from 1.5% to 3% by dry weight,
- caprylyl/capryl glucoside present in a mass percentage ranging from 1% to 40% by dry weight, preferably from 5% to 30% by dry weight, more preferably from 7.5% to 20% by dry weight,
- free gluconic acid present in a mass percentage ranging from 10% to 70% by dry weight, preferably from 20% to 60% by dry weight, more preferably from 25% to 50% by dry weight, and most preferably from 27.5% to 40% by dry weight,
- water present in a mass percentage ranging from 20% to 75% by weight, preferably from 30% to 65% by weight, more preferably from 35% to 55% by weight,
- the percentages by weight being expressed in relation to the total weight of the liquid antimicrobial composition.

According to one embodiment, the antimicrobial liquid consists of:

- essential oil of one of the species of the genus *Cymbopogon* present in a mass percentage ranging from 0.1% to 10% by dry weight, preferably from 0.5% to 7% by dry weight, more preferably from 1% to 5% by dry weight, and most preferentially from 1.5% to 3% by dry weight,
- caprylyl/capryl glucoside present in a mass percentage ranging from 1% to 40% by dry weight, preferably from 5% to 30% by dry weight, and more preferably from 7.5% to 20% by dry weight,
- free gluconic acid present in a mass percentage ranging from 10% to 70% by dry weight, preferably from 20% to 60% by dry weight, more preferably from 25% to 50% by dry weight, and most preferentially from 27.5% to 40% by dry weight,
- water present in a mass percentage ranging from 20% to 75% by weight, or from 30% to 65% by weight, or from 35% to 55% by weight,
- the percentages by weight being expressed in relation to the total weight of the liquid antimicrobial composition,
- the sum of the mass percentages of all the constituents being equal to 100%.

According to one embodiment, the antimicrobial liquid composition to which the present application relates comprises, preferably consists of:

- an essential oil selected from essential oils of clove, citronella, geranium bourbon, geranium grass, lemongrass, lemongrass, West India lemongrass, East India lemongrass, *Litsea citrata*, lemon balm, palmarosa, chili pepper, West India bay, oregano, tea tree, thyme, lemongrass.
- a nonionic surfactant chosen from alkyl(poly)glycosides, preferably from alkyl(poly)glucosides,
- a free carboxylic acid selected from gluconic acid, succinic acid,
- and/or a salt of said carboxylic acid, chosen from the salts of calcium, sodium, potassium, calcium, magnesium, zinc,
- water.

According to one embodiment, the antimicrobial liquid composition of the invention comprises, preferably consists of:

an essential oil chosen from essential citronella oils, and essential oils of West India lemongrass, East India lemongrass, and preferentially from essential oils of species of the genus *Cymbopogon,* a nonionic surfactant chosen from alkyl(poly)glycosides, preferably from alkyl(poly)glucosides, a free carboxylic acid selected from gluconic acid, succinic acid, and/or a salt of said carboxylic acid, chosen from the salts of calcium, sodium, potassium, calcium, magnesium, zinc, According to one embodiment, the antimicrobial liquid composition of the invention comprises, preferably consists of:

essential oil of one of the species of the genus *Cymbopogon,* caprylyl/capryl glucoside, gluconic acid, sodium gluconate, water.

According to one embodiment, the antimicrobial liquid composition comprises:

essential oil of one of the species of the genus *Cymbopogon* present in a mass percentage ranging from 0.1% to 10% by dry weight, preferably from 0.5% to 7% by dry weight, more preferably from 1% to 5% by dry weight, and most preferentially from 1.5% to 3% by dry weight, caprylyl/capryl glucoside present in a mass percentage ranging from 1% to 40% by dry weight, preferably from 5% to 30% by dry weight, more preferably from 7.5% to 20% by dry weight, free gluconic acid present in a mass percentage ranging from 10% to 70% by dry weight, preferably from 20% to 60% by dry weight, more preferably from 25% to 50% by dry weight, and most preferentially from 27.5% to 40% by dry weight, sodium gluconate present in a mass percentage ranging from 1% to 50% by dry weight, preferably from 5% to 30% by dry weight, more preferably from 10% to 20% by dry weight, and most preferentially from 15% to 17.5% by dry weight, water present in a mass percentage ranging from 20% to 75% by weight, preferably from 30% to 65% by weight, more preferably from 35% to 55% by weight, the percentages by weight being expressed in relation to the total weight of the liquid antimicrobial composition.

According to one embodiment, the antimicrobial liquid consists of:

essential oil of one of the species of the genus *Cymbopogon* present in a mass percentage ranging from 0.1% to 10% by dry weight, preferably from 0.5% to 7% by dry weight, more preferably from 1% to 5% by dry weight, and most preferentially from 1.5% to 3% by dry weight, caprylyl/capryl glucoside present in a mass percentage ranging from 1% to 40% by dry weight, preferably from 5% to 30% by dry weight, and more preferably from 7.5% to 20% by dry weight, free gluconic acid present in a mass percentage ranging from 10% to 70% by dry weight, preferably from 20% to 60% by dry weight, more preferably from 25% to 50% by dry weight, and most preferentially from 27.5% to 40% by dry weight, sodium gluconate present in a mass percentage ranging from 1% to 50% by dry weight, preferably from 5% to 30% by dry weight, more preferably from 10% to 20% by dry weight, and most preferentially from 15% to 17.5% by dry weight, water present in a mass percentage ranging from 20% to 75% by weight, or from 30% to 65% by weight, or from 35% to 55% by weight, the percentages by weight being expressed in relation to the total weight of the liquid antimicrobial composition, the sum of the mass percentages of all the constituents being equal to 100%.

The choice of the constituents of the antimicrobial liquid composition to which the present application relates also has the advantage of giving it a content index of natural origin, denoted CNO, of 100% the alkyl(poly)glucosides being obtained only from plant resources.

Structure of the Antimicrobial Composition

The antimicrobial composition to which the present application relates is in the form of a liquid, which is a dispersion of an oily phase in an aqueous phase. This dispersion may be either an oil-in-water emulsion, or an oil-in-water microemulsion, or an oil-in-water nanoemulsion, or a micellar solution, depending on the nature and quantities of the constituents of the composition and its production method. According to one embodiment, the antimicrobial composition is an oil-in-water emulsion, and has droplet sizes of oily phase ranging from 0.3 micrometers to 10 micrometers. According to another embodiment, the antimicrobial composition is an oil-in-water microemulsion or an oil-in-water micellar composition, and has droplet sizes ranging from 0.001 micrometers to 0.3 micrometers. The small sizes of the droplets, or microdroplets or micelles, of the antimicrobial liquid composition make it opalescent or transparent. In addition, they also contribute to improving the stability of the oil in water, and to improve its antimicrobial activity and its effectiveness as a preservative activator.

According to one embodiment, the oily dispersed phase comprises the essential oil; the aqueous phase comprises the carboxylic acid and/or the carboxylic acid salt; and the surfactant is located at the interface between the two phases. The oily phase may comprise a "nonessential" oil, such as triglycerides, in order to adjust the essential oil concentration in the oily phase, and also to reduce the potential allergenic nature of the essential oil. The oily phase may also comprise oils such as methyl esters of plant oils, or short fatty acid triglycerides. The oily phase and the aqueous phase may also comprise additives without antimicrobial activity, such as rheology agents, soluble dyes, pigments, fragrances, humectants, bulking agents.

According to another embodiment, the oily dispersed phase consists of essential oil; the aqueous phase consists of water, free carboxylic acid and/or carboxylic acid salts; and the nonionic surfactant is distributed between the two phases. In this embodiment, the aqueous phase contains, as its one and only solvent, water, and is therefore free of any other solvent, in particular any organic solvent.

Advantageously, the transparency of the antimicrobial liquid composition and compatibility with ionic surfactants allow the addition of this antimicrobial composition to cosmetic products that are themselves transparent, such as micellar water or gels, while maintaining transparency.

Indeed, the antimicrobial liquid composition is in the form of a macroscopically homogeneous liquid, which allows easy use during the production of cosmetic products.

The handling of a liquid requires less personal or collective protective equipment than the handling of a powdery powder. The transfer between container and the precise dosage are also much simpler and more reliable than for a powdery powder.

Thus, the antimicrobial liquid composition can be easily incorporated into a cosmetic product in order to activate the present preservative, without destabilizing the cosmetic product. This composition according to the invention offers good stability and compatibility with cosmetic products, allowing transparency without any problems of crystallization or precipitation.

Cosmetic Product

The present application also relates to a cosmetic product containing as a preservative activator, an antimicrobial liquid composition according to the invention, and at least one standard cosmetic product preservative as previously described.

According to one embodiment, the cosmetic product comprises:

up to 2.5% by gross weight, preferably up to 1.5% by gross weight, more preferably up to 1% by gross weight, preferably up to 0.7% by gross weight, and even more preferably up to 0.6% by gross weight of said at least one preservative, and at least 0.1% by gross weight, preferably at least 0.5% by gross weight, more preferably at least 0.75% by gross weight, preferably at least 1% by gross weight, and even more preferably at least 1.5% by weight of said at least one antimicrobial liquid composition, relative to the total weight of the cosmetic product.

Preferably, the cosmetic product comprises:

up to 0.5% by raw weight, preferably up to 0.4% by weight of said at least one preservative, and at least 2.0% by gross weight, preferably at least 3% by weight of said at least one antimicrobial liquid composition, relative to the total weight of the cosmetic product.

Most preferentially, the cosmetic product comprises:

from 0.1% to 2.5% by gross weight, preferably from 0.2% to 1.5% by gross weight, more preferably from 0.3% to 1% by gross weight, and most preferentially from 0.4% to 0.7% by weight of said at least one preservative, and 0.1% to 5% by gross weight, preferably from 0.5% to 3% by gross weight, more preferably from 0.75% to 2% by weight, crude and most preferentially from 1% to 1.5% by gross weight, of said at least one antimicrobial liquid composition, relative to the total weight of the cosmetic product.

According to one embodiment, the cosmetic product comprises a single antimicrobial liquid composition according to the present application, and a single preservative.

The cosmetic product may be in all known forms or physical states, namely an oil-in-water emulsion, a water-in-oil emulsion, a suspension, a foam, a true solution, a micellar solution, a hydroalcoholic solution, a paste, a gel, a powder, a tablet, a wipe. Preferably, the product is in a form chosen from an oil-in-water emulsion, a water-in-oil emulsion, a suspension, a foam, a true solution, a micellar solution, a hydroalcoholic solution, a paste, a gel. Even more preferentially, the product is in a form chosen from an oil-in-water emulsion, a water-in-oil emulsion, a suspension, a foam, a true solution, a micellar solution, a paste, a gel.

The cosmetic product due to the neutrality of the composition according to the invention and its high compatibility with the very large majority of fatty oils and bodies, alcohols, surfactants, emulsifiers, solubilizers, conditioners, film-forming agents, thickeners, gelling agents, neutralizing agents, or even active ingredients, may be formulated without particular difficulty and very widely with commonly used ingredients.

Method for Preparing an Antimicrobial Liquid Composition According to the Invention The following protocol describes the preparation of an antimicrobial composition consisting of essential oil(s), gluconic acid, sodium gluconate and a solubilizing surfactant. When the solubilizing surfactant is in the form of a powder, it is dissolved in a minimum amount of water. In an open beaker, the required amount of essential oil(s) is added slowly to the required amount of solution of solubilizing surfactant, with gentle stirring (for example 500-1000 rpm with the Rayneri engine equipped with a propeller) and at room temperature (22° C.), until a homogeneous solution is obtained. This aqueous solution of essential oil(s) is added and to solubilize to an aqueous solution of gluconic acid composed of the required amount of free gluconic acid and sodium gluconate, with gentle stirring (for example 500-1000 rpm to the Rayneri engine equipped with a propeller) and at room temperature (22° C.), until a homogeneous solution is obtained.

Used as a preservative activator, the antimicrobial composition can be added to the cosmetic product at the end of preparation, in other words after the product has been prepared, when the preparation of said cosmetic product comprises heating steps at high temperature 60-80° C. over durations exceeding a few minutes. When the preparation of the cosmetic product is done entirely at ambient temperature, the antimicrobial composition can be added from the first preparation steps, but it is preferable to add it at the end of the preparation of the cosmetic product.

Other Possible Applications:

The antimicrobial composition according to the invention can also find out-of-cosmetic uses and may in particular be suitable for microbiologically stabilizing pharmaceutical, food or industrial compositions such as for example liquid detergent compositions, liquid washing compositions, and amylaceous adhesives.

The present application also relates to the use of an antimicrobial composition according to the present application for killing microorganisms, or pathogenic microorganisms, or inhibiting the growth of microorganisms or pathogenic microorganisms, on or in a non-living or artificial substrate. Such an application relates, for example, to the disinfection of surfaces (floors, walls, doors, door handles), disinfection/preservation of industrial liquid products, such as aqueous solutions of starch, protein, or fiber.

EXAMPLES

Example 1: Selection of a Solubilizinq Surfactant to Achieve the Transparency Criteria This example shows the selection of a solubilizing surfactant and the ratio of the raw mass of surfactant to the raw mass of essential oil, to obtain an aqueous solution of lemongrass essential oil *Cymbopogon flexuosus* which is transparent both in the concentrated state and when diluted in water. A solubilizing surfactant will be acceptable if both transparency criteria are satisfied. Only the main surfactants tested that gave results are presented here. The ratio of the gross weight of surfactant to the gross weight of essential oil is denoted "SA/EO gross weight" below.

For each solubilizing surfactant to be tested (Table 1), a liquid composition is prepared with the following masses of constituents:

1.2 grams of gluconic acid (in dry form), 3 grams of demineralized water, 2.4 grams of essential oil of lemongrass "*Cymbopogon flexosus* Oil®" from the supplier Elixens, 14.4 or 19.2 or 24 gross grams, that is, grams of product in its commercially available form, of a solubilizing surfactant in Table 1 (all being nonionic surfactants) in order to achieve a SA/EO gross weight, respectively, of 6, 8 or 10.

The protocol for preparing a liquid composition is as follows.

a first pre-mixture is prepared by dissolving gluconic acid in the mass of water with gentle stirring at 20-22° C., a second pre-mixture is prepared by adding to the essential oil mass, the required mass of solubilizing surfactant, and the mixture is stirred to allow the essential oil to be dispersed and to obtain a homogeneous liquid, the second pre-mixture is then added in the first pre-mixture, and gentle non-shearing stirring is maintained for about 20 minutes, to leave the time for the pre-mixture of surfactant and essential oil to disperse, and thus for the liquid composition to stabilize.

Immediately after the preparation, the state of the liquid composition prepared in order to evaluate its transparency and homogeneity, in particular over the entire height of the sample, is observed with the naked eye and in order to seek the possible presence of several phases or solid particles (which would be formed instantly by precipitation, or more slowly by crystallization). This state is referred to as "concentrated liquid composition". For half of the volume of liquid composition, these observations are continued during storage at temperature of 20-22° C. for 1 month.

In the other half, a dilution behavior test in water is carried out. The liquid composition is diluted 1.5 grams in a water mass of 98.5 grams. The state of the water added to the liquid composition is observed with the naked eye in order to evaluate its transparency and homogeneity, in particular over the entire height of the sample, and to seek the possible presence of several phases or solid particles. This is the "after dilution in water" state. These observations are continued during storage at a temperature of 20-22° C. for 1 month.

For the state of "concentrated composition" and for the "after dilution in water" state, the transparency and homogeneity are qualified and evaluated as follows:

"failure": presence of solid particles, in particular at the bottom of the sample; or presence of at least 2 phases, generally a supernatant, presence of a paste, in particular at the bottom of the sample; light turbidity, visible to the naked eye; heterogeneous transparency, with an upper part and a visible lower part; creamy appearance, in particular ivory.

"success": opalescence virtually imperceptible to the naked eye; homogeneous transparency visible to the naked eye.

The transparency and homogeneity results of the "concentrated liquid composition" are presented in Table 2, and the transparency and homogeneity results "after dilution in water" are presented in Table 3.

TABLE 1

| Ref. | Trade name (supplier) | INCI |
|---|---|---|
| A | Resassol ® Apostrophie (Res Pharma Industriale) | Caprylyl/Capryl Glucoside (and) Water (and) Polyglyceryl-3 Cocoate (and) Polyglyceryl-10 Laurate (and) Citric Acid |
| B | Lamesoft ® OD (BASF) | Coco-Caprylate (and) Lauryl Glucoside (and) Glycerin (and) Polyglyceryl-2 Dipolyhydroxystearate (and) Polyglyceryl-3 Diisostearate |
| C | Symbio ®Solv Clear Plus MB (Evonik Operations GmbH) | Caprylyl/Capryl Glucoside (and) Aqua (and) Sodium Cocoyl Glutamate (and) Glyceryl Caprylate (and) Citric Acid (and) Polyglyceryl-6 Oleate (and) Sodium Surfactin |
| D1 | Tegosoft ® PC 41 (Evonik Operations GmbH) | Polyglyceryl-4 Caprate |
| D2 | Emulpharma ® ECO 10 (Res Pharma Industriale) | Polyglyceryl-10 Laurate (and) water |
| D3 | Polyaldo ® 10-1-CC (Lonza) | Polyglyceryl-10 Caprylate/Caprate |
| D4 | NatraGem ® E145 (Croda) | Polyglyceryl-4 Laurate/Succinate |
| D5 | Decaglyn 10-MAC (Nikkol) | Polyglyceryl-10 Decamacadamiate |
| E | Sepiclear ™ G7 (Seppic) | Heptyl Glucoside |
| F | Oramix ™ CG 110 (Seppic) | Caprylyl/Capryl Glucoside |
| G | Poly Suga ®Mulse D9 (Colonial Chemical Inc.) | Sorbitan Oleate Decylglucoside Crosspolymer |

TABLE 2

| Solubilizing surfactant | Criteria for transparency and homogeneity of the concentrated liquid composition For a value of the SA/EO gross weight equal to: | | |
|---|---|---|---|
| Ref. | 6 | 8 | 10 |
| A | failure | failure | success |
| B | failure | failure | failure |
| C | failure | failure | failure |
| D1 to D5 | failure | failure | failure |
| E | failure | failure | success |
| F | failure | success | success |
| G | failure | failure | failure |

TABLE 3

| Solubilizing surfactant | Criteria for transparency and homogeneity after dilution in water For a value of the SA/EO gross weight equal to: | | |
|---|---|---|---|
| Ref. | 6 | 8 | 10 |
| A | failure | failure | failure |
| B | failure | failure | success |
| C | failure | failure | success |
| D1 to D5 | failure | failure | failure |
| E | failure | failure | failure |
| F | failure | success | success |
| G | success | success | success |

The surfactants A, E and F make it possible to provide a concentrated liquid composition which is transparent.

The surfactants B, C and G fail to provide a concentrated liquid composition that is transparent, but allows transparency after dilution in water. The surfactant F makes it possible to achieve transparency after dilution in water.

Thus, surfactants A, B, C, E, F and G may be suitable for the antimicrobial liquid composition to which the present application relates.

Among all the tests carried out, only the solubilizing surfactant F, that is caprylyl/capryl glucoside, makes it possible to satisfy both the transparency and homogeneity criterion of the concentrated liquid composition, and the same criterion after dilution in water, for the SA/EO gross weight ratio values ranging from 8 to 10. In the case of the non-ionic surfactant solubilizing caprylyl/capryl glucoside, SA/EO gross weight ratio values ranging from 8 to 10 are equivalent to values of a ratio of the dry mass of surfactant to the dry mass of essential oil ranging from 4 to 5 (because this surfactant comprises 50% water and 50% caprylyl/capryl glucoside).

Example 2: Preparations of Antimicrobial Compositions

The ingredients used are presented in Table 4. The compositions of the antimicrobial compositions that are the subject of the present application are presented in Table 5.

TABLE 4

| Trade name (Supplier) | Composition of the commercial product (% weight) |
|---|---|
| Solution of gluconic acid 60/35 (Roquette) | 40% water + 60% dry matter consisting of 65% gluconic acid and 35% sodium gluconate |
| Oramix CG110 (SEPPIC) | 50% caprylyl/capryl glucoside + 50% water |
| *Cymbopogon flexuosus* oil ® (Elixens) | 100% essential oil of lemongrass *Cymbopogon flexuosus* |

TABLE 5

| Trade name (Supplier) | Antimicrobial composition 40 (% weight) | Antimicrobial composition 43 (% weight) |
|---|---|---|
| Solution of gluconic acid 60/35 (Roquette) | 57.13 | 78.00 |
| Oramix CG110 (SEPPIC) | 39.00 | 20.00 |
| Essential oil of lemongrass *Cymbopogon flexuosus* | 3.93 | 2.00 |

The antimicrobial compositions 40 and 43 are prepared according to the following protocol:

In an open beaker, the required amount of essential oil(s) is added slowly to the required amount of solution of solubilizing surfactant, with gentle stirring (for example 500-1000 rpm with the Rayneri engine equipped with a propeller) and at room temperature of 22° C., until a homogeneous solution is obtained. This aqueous solution of essential oil and of solubilizing to an aqueous solution of gluconic acid and sodium gluconate are added.

Example 3: Demonstration of Microbiological Stabilizing Properties

The antibacterial and antifungal activities of the compositions prepared in example 2 are demonstrated through in-vitro growth tests on standard culture media for the following microorganisms: *Escherichia coli* ATCC® 8739, *Pseudomonas aeruginosa* ATCC® 9027, *Staphylococcus aureus* ATCC® 6538, *Candida albicans* ATCC® 10231, and *Aspergillus brasiliensis* ATCC® 16404. These tests comprise comparisons with the constituents of the compositions taken in isolation, and taken in combination with two constituents, in order to identify the antimicrobial activity synergies on these microorganisms.

For each microorganism, one test tube is prepared for each product to be tested, that is the antimicrobial composition, the constituents alone, or the combinations of two constituents, as well as a control, with the culture medium; adapted to the microorganism: "potato dextrose broth" for *Aspergillus brasiliensis*; "yeast molds" for *Candida albicans*, "tryptone soy broth" for *Escherichia coli*; "medium" for *Staphylococcus aureus*; and "medium" for *Pseudomonas aeruginosa*. Dose of product to be tested according to Table 6 below, expressed in percentage weight/volume, is then added in each test tube. For example, a percentage of 1.5% by weight/volume means that, for 100 mL of culture medium, 1.5 g of product to be tested is added. Next, the solution is carefully homogenized with suction-discharge cycles.

TABLE 6

| Test reference | Product to be tested | Series "composition 40" (% w/v) | Series "composition 43" (% w/v) |
|---|---|---|---|
| Control | Water | 1.5 | 1.5 |
| A | Solution of gluconic Acid 60/35 | 0.857 | 1.17 |
| B | Oramix CG110 | 0.585 | 0.3 |
| C | Essential oil of lemongrass *Cymbopogon flexuosus* | 0.059 | 0.03 |
| D | Solution of gluconic Acid 60/35 + Oramix CG110 | 0.857 + 0.585 | 1.17 + 0.3 |
| E | Solution of gluconic Acid 60/35 + Essential oil of lemongrass *Cymbopogon flexuosus* | 0.857 + 0.059 | 1.17 + 0.03 |
| F | Oramix CG110 + Essential oil of lemongrass *Cymbopogon flexuosus* | 0.585 + 0.059 | 0.3 + 0.03 |
| G | Composition 40 | 1.50 | — |
| H | Composition 43 | — | 1.5 |

Each test tube is inoculated with a known amount of microorganisms: 10^3 colony-forming units per milliliter of agar (denoted CFU/mL) for *Aspergillus brasiliensis;* 10^4 CFU/mL for *Escherichia coli* and *Candida albicans,* 10^5 CFU/mL for *Staphylococcus aureus* and *Pseudomonas aeruginosa*. At the end of the inoculation, the inoculated media are again carefully homogenized by suction-discharge cycles.

The samples inoculated with *Aspergillus brasiliensis* are incubated at 30° C. (+/−2.5° C.) for 48 hours. The samples inoculated with the other strains are incubated at 37° C. (+/−2.5° C.) for 48 hours.

The microorganisms are sampled and counted at 30 minutes, 24 hours and 48 hours for each microorganism. The inoculated samples are sampled, diluted in series in diluant (Peptone of casein 1 g/L, sodium chloride 8.5 g/L, pH 7, and deposited respectively on potato and dextrose geloses for *Aspergillus brasiliensis*, trypto-caseine-soy agars for *Escherichia coli* and Sabouraud dextrose agars for *Candida albicans*. The agars are incubated for 24 to 72 hours before counting the colonies present.

The measurements of microorganisms taken at each collection time are expressed as CFUs/mL. The detection limit of the test of 100 CFU/mL.

The results of the conducted tests are presented in Table 7 for *Escherichia coli*, in Table 8 for *Candida albicans*, in Table 9 for *Aspergillus brasiliensis*, in Table 10 for *Staphylococcus aureus*, and in Table 11 for *Pseudomonas aeruginosa*.

TABLE 7

| *E. Coli* | | | | |
|---|---|---|---|---|
| Reference product to | Count (CFU/mL) | | | |
| be tested | 0 hours | 0.5 hours | 24 hours | 48 hours |
| Control | 3.5 × 10^4 | 3.5 × 10^4 | 5.6 × 10^8 | 4.0 × 10^8 |
| A | 3.5 × 10^4 | 3.5 × 10^4 | 4.0 × 10^8 | 2.9 × 10^8 |
| B | 3.5 × 10^4 | 2.0 × 10^3 | 2.7 × 10^7 | 5.8 × 10^5 |
| C | 3.5 × 10^4 | 3.0 × 10^3 | 4.1 × 10^7 | 7.0 × 10^4 |
| D | 3.5 × 10^4 | 6.0 × 10^2 | 3.2 × 10^6 | 1.8 × 10^6 |
| E | 3.5 × 10^4 | 3.7 × 10^4 | 1.0 × 10^8 | 1.7 × 10^7 |
| F | 3.5 × 10^4 | 1.0 × 10^2 | 1.0 × 10^2 | 1.0 × 10^1 |
| G | 3.5 × 10^4 | 1.0 × 10^2 | 1.0 × 10^2 | 1.0 × 10^1 |
| H | 3.5 × 10^4 | 4.0 × 10^2 | 1.0 × 10^2 | 1.0 × 10^1 |

TABLE 8

| *C. Albicans* | | | | |
|---|---|---|---|---|
| Reference product to | Count (CFU/mL) | | | |
| be tested | 0 hours | 0.5 hours | 24 hours | 48 hours |
| Control | 2.0 × 10^4 | 2.0 × 10^4 | 9.5 × 10^6 | 8.5 × 10^6 |
| A | 2.0 × 10^4 | 2.4 × 10^4 | 9.3 × 10^6 | 5.9 × 10^6 |
| B | 2.0 × 10^4 | 1.9 × 10^4 | 4.7 × 10^5 | 4.3 × 10^5 |
| C | 2.0 × 10^4 | 1.5 × 10^4 | 1.0 × 10^2 | 1.0 × 10^2 |
| D | 2.0 × 10^4 | 1.9 × 10^4 | 9.7 × 10^3 | 7.1 × 10^4 |
| E | 2.0 × 10^4 | 2.2 × 10^4 | 1.0 × 10^2 | 1.0 × 10^2 |
| F | 2 × 10^4 | 1.8 × 10^4 | 1.0 × 10^2 | 1.0 × 10^2 |
| G | 2.0 × 10^4 | 1.4 × 10^4 | 1.0 × 10^2 | 1.0 × 10^2 |
| H | 2.0 × 10^4 | 2.7 × 10^4 | 1.0 × 10^2 | 1.0 × 10^2 |

TABLE 9

| *A. Brasiliensis* | | | | |
|---|---|---|---|---|
| Reference product to | Count (CFU/mL) | | | |
| be tested | 0 hours | 0.5 hours | 24 hours | 48 hours |
| Control | 3.0 × 10^3 | 3.0 × 10^3 | 1.1 × 10^4 | 1.0 × 10^3 |
| A | 3.0 × 10^3 | 6.4 × 10^3 | 2.5 × 10^3 | 1.0 × 10^3 |
| B | 3.0 × 10^3 | 5.1 × 10^3 | 4.0 × 10^2 | 8.0 × 10^2 |
| C | 3.0 × 10^3 | 4.2 × 10^3 | 1.0 × 10^2 | 1.0 × 10^2 |
| D | 3.0 × 10^3 | 7.6 × 10^3 | 2.0 × 10^2 | 1.0 × 10^2 |
| E | 3.0 × 10^3 | 5.1 × 10^3 | 2.2 × 10^3 | 3.0 × 10^3 |
| F | 3.0 × 10^3 | 6.5 × 10^3 | 1.0 × 10^2 | 1.0 × 10^2 |
| G | 3.0 × 10^3 | 7.3 × 10^3 | 1.0 × 10^2 | 1.0 × 10^2 |
| H | 3.0 × 10^3 | 6.2 × 10^3 | 1.0 × 10^2 | 1.0 × 10^2 |

TABLE 10

| *S. Aureus* | | | | |
|---|---|---|---|---|
| Reference product to | Count (CFU/mL) | | | |
| be tested | 0 hours | 0.5 hours | 24 hours | 48 hours |
| Control | 8.6 × 10^4 | 7.1 × 10^4 | 1.3 × 10^8 | 2.9 × 10^8 |
| A | 8.6 × 10^4 | 1.1 × 10^5 | 5.2 × 10^4 | 4.2 × 10^4 |
| B | 8.6 × 10^4 | 1.2 × 10^5 | 1.3 × 10^7 | 1.4 × 10^7 |
| C | 8.6 × 10^4 | 1.3 × 10^5 | 3.4 × 10^5 | 1.2 × 10^6 |
| D | 8.6 × 10^4 | 9.4 × 10^4 | 2.0 × 10^2 | 1.0 × 10^2 |
| E | 8.6 × 10^4 | 4.4 × 10^4 | 1.0 × 10^2 | 1.0 × 10^2 |
| F | 8.6 × 10^4 | 5.1 × 10^4 | 2.0 × 10^2 | 1.0 × 10^2 |
| G | 8.6 × 10^4 | n.d. | n.d. | n.d. |
| H | 8.6 × 10^4 | 8.4 × 10^4 | 1.0 × 10^2 | 1.0 × 10^2 |

TABLE 11

| *P. Aeruginosa* | | | | |
|---|---|---|---|---|
| Reference product to | Count (CFU/mL) | | | |
| be tested | 0 hours | 0.5 hours | 24 hours | 48 hours |
| Control | 3.6 × 10^5 | 5.1 × 10^5 | 3.8 × 10^8 | 4.0 × 10^8 |
| A | 3.6 × 10^5 | 5.6 × 10^5 | 8.7 × 10^6 | 4.8 × 10^8 |
| B | 3.6 × 10^5 | 1.2 × 10^6 | 1.6 × 10^7 | 1.5 × 10^7 |
| C | 3.6 × 10^5 | 6.5 × 10^5 | 1.3 × 10^8 | 1.5 × 10^8 |
| D | 3.6 × 10^5 | 4.6 × 10^5 | 2.1 × 10^3 | 1.0 × 10^2 |
| E | 3.6 × 10^5 | 4.6 × 10^5 | 4.1 × 10^8 | 3.8 × 10^8 |
| F | 3.6 × 10^5 | 7.3 × 10^5 | 2.0 × 10^7 | 1.0 × 10^7 |
| G | 3.6 × 10^5 | n.d. | n.d. | n.d. |
| H | 3.6 × 10^5 | 3.7 × 10^5 | 6.7 × 10^3 | 4.0 × 10^2 |

All these results show that compositions 40 and 43 have antibacterial and antifungal properties under in vitro culture conditions on agar media, since they make it possible to microbiologically stabilize culture media inoculated with reference bacteria and fungi over durations ranging up to 48 hours.

Advantageously still, the antimicrobial compositions retain their antifungal and antibacterial properties once integrated into cosmetic compositions.

Example 4: Activation of Preservatives at pH 6 in an Oil-In-Water Emulsion

In this example, the capacity of composition 43 prepared in example 3, to be activated, and the bactericidal and fungicidal activity of preservatives at pH 6 in an oil-in-water emulsion, are demonstrated. The preservatives are phenoxyethanol, benzyl alcohol, sodium benzoate, and potassium sorbate. They are listed in Appendix 5 of Regulation No. 1223/2009.

The cosmetic product used for this demonstration is an oil-in-water emulsion cream, called "cotton cream". Creams are prepared according to the composition of Table 12, by adding the sufficient amounts, denoted "Qs", of composition 43 and of preservative according to the values of Table 10. Efficacy tests of the antimicrobial protection are carried out on each cream in Table 13 for the five microorganisms of the standard ISO 11930:2019 *Pseudomonas aeruginosa, Staphylococcus aureus, Escherichia coli, Candida albicans, Aspergillus brasiliensis*.

TABLE 12

| Phase | Ingredient/Supplier | INCI | % wt emulsion |
|---|---|---|---|
| A | Emulium delta/ Gattefossé | Cetyl Alcohol, Glyceryl Stearate, PEG-75 Stearate, Ceteth-20, Steareth-20 | 5.00 |
| A | Caprylis/Aromazone (ou Myritol 312/BASF Care Creations) | Caprylic/capric triglycerides | 10.00 |
| A | Sweet almond oil/Cooper oil | Sweet almond oil | 10.00 |
| A | Cetyl alcohol/Cooper | Cetyl alcohol | 2.00 |
| B | Beauté by Roquette ® ST 012 | | 1.50 |
| C | Demineralized water | Aqua | q.s. 100 |
| C | Xanthan Gum FNCSP-PC/Jungbunzlauer (ou Keltrol CG-SFT/CP Kelco) | Xanthan gum | 0.30 |
| D | Composition 43 | — | Qs according to test |
| D | Preservative | — | Qs according to test |
| E | 10% MS soda | Soda | Qs pH 6 |

In order to prepare the cream of Table 9, all the ingredients of phase A are mixed, and are heated to 75° C. Keeping them at 75° C., phase B is added to phase A with gentle stirring (500-750 rpm; marine propeller), followed by waiting until the mixture is homogeneous. Phase A+B is then added in phase C with emulsifying stirring (3000 rpm; deflocculator) for 10 minutes, keeping it at 75° C. It is allowed to cool to 45° C., and phase D is added with medium stirring (1500 rpm; marine propeller). The mixture is cooled to 25° C. with gentle stirring (500-750 rpm; marine propeller), then the pH is finally adjusted to 6 with phase E.

TABLE 13

| Cream no. | Qs of composition 43 (% wt emulsion) | Qs of preservative (% wt emulsion) |
|---|---|---|
| 1 | 0% | 0% |
| 2 | 0% | 1% Microcare ® PM4 (Thor) |
| 3 | 1% | 0% |
| 4 | 1.5% | 0% |
| 5 | 0% | 0.4% phenoxyethanol |
| 6 | 1% | 0.4% phenoxyethanol |
| 7 | 0% | 0.4% benzyl alcohol |
| 8 | 1% | 0.4% benzyl alcohol |
| 9 | 0% | 0.4% sodium benzoate |
| 10 | 1% | 0.4% sodium benzoate |
| 11 | 0% | 0.4% potassium sorbate |
| 12 | 1% | 0.4% potassium sorbate |

Each antimicrobial protection efficacy test is conducted according to the guidelines of the ISO 11930:2019 standard. The results are presented in Tables 14 to 19. They are expressed as a logarithmic reduction in numbers of colony-forming units per mL. A positive value corresponds to a decrease in the number of colony-forming units. A negative value corresponds to an increase in the number of colony-forming units.

TABLE 14

| Microorganisms | Time | Cream 1: White without preservative | Cream 2: 1% Microcare ® PM4 (Thor) |
|---|---|---|---|
| *Pseudomonas* | 7 days | <−0.63 | 0.68 |
| *Aeruginosa* | 14 days | −2.63 | 3.14 |
| | 28 days | −0.26 | 3.75 |
| *Staphylococcus* | 7 days | 1.91 | 2.11 |
| *Aureus* | 14 days | 4.74 | >4.92 |
| | 28 days | >4.92 | >4.92 |
| *Escherichia Coli* | 7 days | <−0.63 | >4.85 |
| | 14 days | −0.16 | >4.85 |
| | 28 days | −0.29 | >4.85 |
| *Candida Albicans* | 7 days | <−0.60 | 0.6 |
| | 14 days | −1.67 | 1.41 |
| | 28 days | −1.41 | 3.40 |
| *Aspergillus* | 14 days | 0.27 | 0.35 |
| *Brasiliensis* | 28 days | 0.17 | 1.36 |

The antimicrobial protection measurement of cream 1, which is a cream without any preservative and without a preservative activator, shows that cream 1 is not protected against *Pseudomonas aeruginosa, Escherichia coli*, and *Candida albicans*, but is protected against *Staphylococcus aureus* and *Aspergillus brasiliensis* (the term self-protection) beyond 14 days. This measurement constitutes our negative control.

The measurement of the antimicrobial protection of cream 2, which contains 1% by weight of the preservative Microcare® PM4 from Thor, is protected against all five microorganisms. This measurement constitutes our positive control.

TABLE 15

| Microorganisms | Time | Cream 3: 1% composition 43 | Cream 4: 1.5% composition 43 |
|---|---|---|---|
| *Pseudomonas* | 7 days | 0.74 | <−0.63 |
| *Aeruginosa* | 14 days | −1.38 | −1.6 |
| | 28 days | −0.84 | −0.95 |
| *Staphylococcus* | 7 days | 2.26 | >4.92 |
| *Aureus* | 14 days | >4.92 | >4.92 |
| | 28 days | >4.92 | >4.92 |
| *Escherichia Coli* | 7 days | 0.2 | <−0.63 |
| | 14 days | 2.33 | −1.14 |
| | 28 days | >4.85 | >4.85 |
| *Candida Albicans* | 7 days | <−0.60 | <−0.60 |
| | 14 days | −2.16 | −1.65 |
| | 28 days | −1.72 | −2.19 |
| *Aspergillus* | 14 days | 0.47 | 0.15 |
| *Brasiliensis* | 28 days | 0.15 | 0.06 |

The antimicrobial protection measures of creams 3 and 4, which respectively contain 1% and 1.5% composition 43, and no preservative, show that none of these creams is protected against *Pseudomonas aeruginosa* and *Candida albicans*. The self-protection against *Staphylococcus aureus* and *Aspergillus brasiliensis* is maintained. Regarding *Escherichia coli*, protection is observed beginning at 28 days. Composition 43 does not make it possible to protect the cream against microbial development. However, it is notable that composition 43 does not degrade the cream's self-protection against *Staphylococcus aureus* and *Aspergillus brasiliensis*.

TABLE 16

| Microorganisms | Time | Cream 5: 0.4% phenoxyethanol | Cream 6: 1% composition 43 + 0.4% phenoxyethanol |
|---|---|---|---|
| *Pseudomonas* | 7 days | −0.05 | 2.69 |
| *Aeruginosa* | 14 days | 0.96 | 4.01 |
| | 28 days | 4.92 | 2.76 |
| *Staphylococcus* | 7 days | 1.38 | >4.92 |
| *Aureus* | 14 days | 2.33 | >4.92 |
| | 28 days | 4.92 | >4.92 |
| *Escherichia Coli* | 7 days | 2.11 | >4.88 |
| | 14 days | 2.89 | >4.88 |
| | 28 days | 3.05 | >4.88 |
| *Candida Albicans* | 7 days | <−0.64 | <−0.64 |
| | 14 days | −0.87 | −0.85 |
| | 28 days | −0.82 | −0.93 |
| *Aspergillus* | 14 days | 0.46 | 2.20 |
| *Brasiliensis* | 28 days | 0.22 | 2.16 |

As regards cream 5, the microbial protection conferred by 0.4% by weight of phenoxyethanol makes it possible to protect the cream but insufficiently, in particular from *Candida albicans* whose population was able to grow in number and seems stabilized, and from *Aspergillus brasiliensis* whose population is somewhat smaller in number, and less so than the positive control.

As regards cream 6, which contains 0.4% by weight of phenoxyethanol and 1% by weight of composition 43, it is found that the microbial protection against *Pseudomonas aeruginosa, Escherichia coli*, and *Aspergillus brasiliensis* is much better than that of cream 5, and equivalent to the positive control. Indeed, from 7 days, or 14 days for *Aspergillus brasiliensis*, high logarithmic reductions are measured, and are greater than the reductions measured on cream 5 by at least 2 log. These reductions continue or hold at 14 days and 28 days for *Escherichia coli* and *Aspergillus brasiliensis*, but not for *Pseudomonas aeruginosa*, whose population was able to grow by about one logarithm between 14 days and 28 days. Self-protection against *Staphylococcus aureus* is maintained. The cream 6 is not, however, protected against *Candida albicans*, which continues to expand.

Advantageously, composition 43 therefore makes it possible to activate the preservative power of phenoxyethanol with respect to *Pseudomonas aeruginosa, Escherichia coli, Aspergillus brasiliensis* and *Staphylococcus aureus*.

TABLE 17

| Microorganisms | Time | Cream 7: 0.4% benzyl alcohol | Cream 8: 1% composition 43 + 0.4% benzyl alcohol |
|---|---|---|---|
| *Pseudomonas* | 7 days | −0.1 | 3.22 |
| *Aeruginosa* | 14 days | 0.72 | >4.92 |
| | 28 days | 4.92 | >4.92 |
| *Staphylococcus* | 7 days | 1.36 | >4.92 |
| *Aureus* | 14 days | 2.42 | >4.92 |
| | 28 days | 4.92 | >4.92 |
| *Escherichia Coli* | 7 days | 0.27 | 1.19 |
| | 14 days | 0.94 | 14.88 |
| | 28 days | 0.77 | 4.88 |
| *Candida Albicans* | 7 days | <−0.64 | <−0.64 |
| | 14 days | −0.89 | −1.29 |
| | 28 days | −0.7 | −0.77 |
| *Aspergillus* | 14 days | 0.01 | 0.46 |
| *Brasiliensis* | 28 days | 0.23 | 0.28 |

Regarding cream 7, the microbial protection conferred by 0.4% by weight of benzyl alcohol does not protect the cream. In particular, benzyl alcohol degrades the self-protection of the cotton cream against *Staphylococcus aureus* greatly (by more than 2 log at 14 days).

As regards cream 8, which contains 0.4% by weight of benzyl alcohol and 1% by weight of composition 43, it is found that the microbial protection against *Pseudomonas aeruginosa, Escherichia coli*, and *Staphylococcus aureus* is much better than that of cream 7, and equivalent to the positive control. Indeed, from 7 days, or 14 days, significant or strong logarithmic reductions are measured, and are greater than the reductions measured for cream 7, by at least 2 log for *Pseudomonas aeruginosa* and *Escherichia coli* and *Staphylococcus aureus*. These reductions continue or remain at 14 days and at 28 days. The cream 8 is not, however, protected against *Candida albicans*, which continues to expand.

Advantageously, the composition 43 therefore makes it possible to activate the preservative power of the benzyl alcohol with respect to *Pseudomonas aeruginosa, Escherichia coli*, and *Staphylococcus aureus*.

TABLE 18

| Microorganisms | Time | Cream 9: 0.4% sodium benzoate | Cream 10: 1% composition 43 + 0.4% sodium benzoate |
|---|---|---|---|
| *Pseudomonas* | 7 days | 1.38 | 3.21 |
| *Aeruginosa* | 14 days | 1.69 | 4.92 |
| | 28 days | 4.92 | 4.92 |
| *Staphylococcus* | 7 days | 1.02 | 3.52 |
| *Aureus* | 14 days | 3.28 | 4.92 |
| | 28 days | 4.92 | 4.92 |
| *Escherichia Coli* | 7 days | 0.78 | 1.06 |
| | 14 days | 1.23 | 4.88 |
| | 28 days | 4.88 | 4.88 |
| *Candida Albicans* | 7 days | <−0.64 | 0.82 |
| | 14 days | −0.96 | 1.24 |
| | 28 days | −0.97 | 2.86 |
| *Aspergillus* | 14 days | 0.48 | 1.14 |
| *Brasiliensis* | 28 days | 0.62 | 1.62 |

As regards the cream 9, the microbial protection conferred by 0.4% by weight of sodium benzoate makes it possible to weakly protect the cream, except against *Candida albicans*. Sodium benzoate slightly degrades the self-protection of the cotton cream against *Staphylococcus aureus*.

As regards cream 10, which contains 0.4% by weight of sodium benzoate and 1% by weight of composition 43, it is found that the microbial protection against *Pseudomonas aeruginosa, Staphylococcus aureus, Escherichia coli, Aspergillus brasiliensis* and *Candida albicans* is much better than that of cream 9, and equivalent to the positive control. Indeed, from 7 days, or 14 days for *A. brasiliensis*, significant or strong logarithmic reductions are measured, and are greater than the reductions measured for cream 7 by at least 1 or 2 log. These reductions continue or remain at 14 days and 28 days. Self-protection against *Staphylococcus aureus* is maintained. It is notable that cream 10 here has sufficient protection against *Candida albicans*.

Composition 43 therefore makes it possible to activate the preservative power of sodium benzoate with respect to *Pseudomonas aeruginosa, Staphylococcus aureus, Escherichia coli, Aspergillus brasiliensis*, and *Candida albicans*. The combination of 1% (by weight) of the composition 43 and of 0.4% (by weight) of sodium benzoate makes it possible to stabilize the cream according to criterion B of the ISO 11930:2019 standard.

TABLE 19

| Microorganisms | Time | Cream 11: 0.4% potassium sorbate | Cream 12: 1% composition 43 + 0.4% of potassium sorbate |
|---|---|---|---|
| *Pseudomonas* | 7 days | 1.78 | 4.92 |
| *Aeruginosa* | 14 days | −0.56 | 4.92 |
| | 28 days | −0.2 | 4.92 |
| *Staphylococcus* | 7 days | 2.74 | 4.92 |
| *Aureus* | 14 days | 14.92 | 4.92 |
| | 28 days | 4.92 | 4.92 |
| *Escherichia Coli* | 7 days | 1.19 | 4.88 |
| | 14 days | 3.67 | 4.88 |
| | 28 days | 4.88 | 4.88 |
| *Candida Albicans* | 7 days | 0.86 | 2.24 |
| | 14 days | 1.23 | 3.84 |
| | 28 days | 0.05 | 3.84 |
| *Aspergillus* | 14 days | 0.96 | 3.82 |
| *Brasiliensis* | 28 days | 1.1 | 3.82 |

As regards cream 11, microbial protection provided by 0.4% by weight of potassium sorbate makes it possible to protect the cream in a manner equivalent to the positive control, except against *Pseudomonas aeruginosa* (from 7 days), *Escherichia coli* (at 7 days) and *Candida albicans* (at 28 days).

As regards cream 12, which contains 0.4% by weight of potassium sorbate and 1% by weight of composition 43, it is found that microbial protection against *Pseudomonas aeruginosa, Staphylococcus aureus, Escherichia coli, Candida albicans* and *Aspergillus brasiliensis* is much better than that of cream 11, and even better than that of the positive control cream 2 (containing 1% of Microcare® PM4). Indeed, from 7 days, or 14 days for *Aspergillus brasiliensis*, high logarithmic reductions are measured, and are greater than the reductions measured on cream 11 by at least 2 log. These reductions continue or remain at 14 days and 28 days.

Advantageously, the composition 43 therefore makes it possible to activate the preservative power of potassium sorbate with respect to *Pseudomonas aeruginosa, Escherichia coli, Candida albicans, Staphylococcus aureus* and *Aspergillus brasiliensis*. The combination of 1% (by weight) of the composition 43 and of 0.4% (by weight) of potassium sorbate makes it possible to stabilize the cream according to criterion A of the ISO 11930:2019 standard.

Example 5: Cosmetic Products Comprising the "Preservative Activator" Composition and a Preservative Product 1: Shampoo

TABLE 22

| Phase | Ingredient (Supplier) | INCI | % wt emulsion |
|---|---|---|---|
| A | Water | Aqua | q.s. 100 |
| A | Keltrol CG-SFT (CP Kelco) | Xanthan gum | 1.00 |
| B | Plantacare 818 UP BASF) | Coco-Glucoside and aqua | 28.80 |
| B | Imwitor 948 (IOI Oleo GmbH) | Glyceryl Oleate | 1.00 |
| B | Microcare Silicone E 1200 (Thor) | PEG-12 Dimethicone | 1.00 |
| C | Composition 43 | | 1.00 |
| C | | Potassium sorbate | 0.40 |
| D | | Citric acid | QS pH 4.8 |

A shampoo is prepared according to the composition of Table 22:

Xanthan gum is added to water with medium stirring until a homogeneous gel is obtained, after approximately 20 minutes of stirring. At a temperature of 20-22° C., the ingredients of phase B are successively added, with medium stirring. Phase C is then added, still with gentle stirring. The pH is then adjusted to 4.8 with citric acid, even with gentle stirring; a transparent and foaming fluid gel is obtained. The Brookfield viscosity at 20-rpm 20° C. for 1 minute (with the mobile RV M04) is 3200 mPa·s+/−500. Composition 43 is therefore very compatible with the shampoo ingredients. Other shampoos are prepared by changing the nature of the ingredients of phase C according to Table 23.

TABLE 23

| Shampoo | Potassium hydroxide (% by weight in the shampoo) | Composition 43 (% by weight in the shampoo) |
|---|---|---|
| Control | 0 | 0 |
| 1 | 0.4 | 0 |
| 2 | 0 | 1.0 |
| 3 | 0.4 | 1.0 |

Efficacy tests of the antimicrobial protection are carried out on each shampoo in Table 23 for the five microorganisms of the standard ISO 11930:2019 *Pseudomonas aeruginosa, Staphylococcus aureus, Escherichia coli, Candida albicans, Aspergillus brasiliensis*. The results are presented in Table 24.

TABLE 24

| Microorganism | Time | Control shampoo | Shampoo 1 | Shampoo 2 | Shampoo 3 |
|---|---|---|---|---|---|
| *Pseudomonas* | 7 days | −0.60 | 3.44 | −0.60 | 4.88 |
| *Aeruginosa* | 14 days | −1.31 | 4.88 | −0.81 | 4.88 |
| | 28 days | −1.03 | 4.88 | −1.18 | 4.92 |
| *Staphylococcus* | 7 days | 3.12 | 4.92 | 3.03 | 4.92 |
| *Aureus* | 14 days | 4.92 | 4.92 | 4.92 | 4.92 |
| | 28 days | 4.92 | 4.92 | 4.92 | 4.92 |
| *Escherichia* | 7 days | 4.80 | 0.03 | 4.80 | 0.17 |
| *Coli* | 14 days | 4.80 | 0.69 | 4.80 | 4.80 |
| | 28 days | 4.80 | 4.80 | 4.80 | 4.80 |

TABLE 24-continued

| Microorganism | Time | Control shampoo | Shampoo 1 | Shampoo 2 | Shampoo 3 |
|---|---|---|---|---|---|
| *Candida* | 7 days | −0.36 | 3.82 | −0.43 | 3.82 |
| *Albicans* | 14 days | −0.83 | 3.82 | −0.79 | 3.82 |
| | 28 days | −1.14 | 3.82 | −1.03 | 3.82 |
| *Aspergillus* | 14 days | −0.45 | 0.91 | −0.57 | 0.99 |
| *Brasiliensis* | 28 days | −0.63 | 2.37 | −0.70 | 2.37 |

With regard to the results of Table 24, it is found that the control shampoo formula is self-protected against *Staphylococcus aureus* and *Escherichia coli*. In shampoo 1, potassium sorbate, which is a listed preservative, exerts a protective effect against three microorganisms *Pseudomonas aeruginosa, Candida albicans* and *Aspergillus brasiliensis*, but causes the loss of the formula's self-protection against *Escherichia coli*, making it not protected against that bacterium. In shampoo 2, wherein the 0.4% of potassium sorbate were substituted by 1% of composition 43, the three strains *Pseudomonas aeruginosa, Candida albicans* and *Aspergillus Brasiliensis* can develop, but not *Escherichia coli*, the reduction of which is 4.80 log from seven days. In this shampoo formula, composition 43 therefore makes it possible to exert a targeted antibacterial activity on the strain *Escherichia coli* effective from seven days and up to 28 days.

In shampoo 3, which contains 0.4% potassium sorbate and 1% composition 43, antimicrobial effects on *Pseudomonas aeruginosa, Candida albicans* and *Aspergillus brasiliensis* are found, and also the antibacterial effect on *Escherichia coli* effective from 14 days and up to 28 days. Composition 43 thus makes it possible to protect the shampoo against the development of bacteria of the genus *Escherichia coli*, and does so without reducing or disrupting antimicrobial activity of the preservative that is potassium sorbate, but rather by activating the antimicrobial activity of potassium sorbate with respect to *Escherichia coli* at 14 days with a reduction of more than 4 logs greater than the reduction allowed by potassium sorbate alone.

The invention claimed is:

1. A method for activating cosmetic product preservatives, comprising the step of incorporating an antimicrobial liquid composition into a cosmetic product containing preservatives, wherein the antimicrobial liquid composition comprises:

*Cymbopogon* essential oil in a mass percentage ranging from 0.1% to 10% by dry weight, caprylyl/capryl glucoside in a mass percentage ranging from 1% to 40% by dry weight, gluconic acid in a mass percentage of from 10% to 70% by dry weight, and sodium gluconate in a mass percentage ranging from 1% to 50% by dry weight, the percentages by weight being expressed in relation to the total weight of the liquid antimicrobial composition;

wherein the preservatives are chosen from benzyl alcohol, potassium sorbate, phenoxyethanol, and sodium benzoate or a mixture thereof.

2. The method according to claim 1, wherein the essential oil is selected from *Cymbopogon flexuosus* Stapf. and *Cymbopogon citrulatus* (DC.) Stapf.

3. The method according to claim 1, wherein the ratio of the total dry mass of caprylyl/capryl glucoside to the total dry mass of essential oils is greater than or equal to 2.

4. A cosmetic product comprising:

at least one preservative selected from sodium benzoate, potassium sorbate, phenoxyethanol, benzyl alcohol or a mixture thereof, wherein the preservative is present up to 2.5% by gross weight relative to the total weight of the cosmetic product, and at least 1% by gross weight of an antimicrobial liquid composition relative to the total weight of the cosmetic product, wherein the antimicrobial liquid composition comprises:

essential oil of one of the species of the genus *Cymbopogon* is present in a mass percentage ranging from 0.1% to 10% by dry weight, caprylyl/capryl glucoside is present in a mass percentage ranging from 1% to 40% by dry weight, gluconic acid is present in a mass percentage of from 10% to 70% by dry weight, sodium gluconate is present in a mass percentage ranging from 1% to 50% by dry weight, water has a mass percentage ranging from 20% to 75% by weight, the percentages by weight being expressed in relation to the total weight of the liquid antimicrobial composition.

5. The cosmetic product according to claim 4, wherein it is in the form of an oil-in-water emulsion, or a water-in-oil emulsion, or an aqueous suspension, or an aqueous foam, or a true aqueous solution, or a micellar solution, or a hydroalcoholic solution, or a paste, or a gel, or a powder, or a tablet, or a wipe.

6. The method according to claim 1, characterized in that said gluconic acid is divided into at most 35% by dry weight of the sodium gluconate of said gluconic acid and at least 65% by dry weight of said gluconic acid.

7. The method according to claim 1, further comprises water at a mass percentage ranging from 20% to 75% by weight, the percentage by weight being expressed in relation to the total weight of the liquid antimicrobial composition.

* * * * *